(12) United States Patent
Rao et al.

(10) Patent No.: US 9,353,373 B2
(45) Date of Patent: May 31, 2016

(54) **BI-FUNCTIONAL SHORT-HAIRPIN RNA (BI-SHRNA) SPECIFIC FOR SINGLE-NUCLEOTIDE *KRAS* MUTATIONS**

(71) Applicant: GRADALIS, Inc., Carrollton, TX (US)

(72) Inventors: Donald Rao, Dallas, TX (US); Zhaohui Wang, Grapewine, TX (US); John J. Nemunaitis, Cedar Hill, TX (US); Neal Senzer, Dallas, TX (US)

(73) Assignee: STRIKE BIO, INC., Dallas, TX (US)

( * ) Notice: Subject to any disclaimer, the term of this patent is extended or adjusted under 35 U.S.C. 154(b) by 309 days.

(21) Appl. No.: 13/890,957

(22) Filed: May 9, 2013

(65) Prior Publication Data
US 2013/0302407 A1 Nov. 14, 2013

Related U.S. Application Data

(60) Provisional application No. 61/644,875, filed on May 9, 2012.

(51) Int. Cl.
| | | |
|---|---|---|
| *C12N 15/113* | (2010.01) | |
| *A61K 31/713* | (2006.01) | |
| *A61K 45/06* | (2006.01) | |
| *C12Q 1/68* | (2006.01) | |

(52) U.S. Cl.
CPC .......... *C12N 15/1135* (2013.01); *A61K 31/713* (2013.01); *A61K 45/06* (2013.01); *C12Q 1/6897* (2013.01); *C12N 2310/51* (2013.01); *C12N 2310/533* (2013.01); *C12N 2320/32* (2013.01); *C12N 2320/50* (2013.01)

(58) Field of Classification Search
CPC .................................................. C12N 15/1135
See application file for complete search history.

(56) References Cited

U.S. PATENT DOCUMENTS

| | | | | |
|---|---|---|---|---|
| 8,735,058 | B2 * | 5/2014 | Rao ................................. | 435/6.1 |
| 2009/0011040 | A1 * | 1/2009 | Naash et al. ................... | 424/501 |

FOREIGN PATENT DOCUMENTS

| | | | |
|---|---|---|---|
| WO | 2009108217 | A2 | 9/2009 |
| WO | 2011053660 | A2 | 5/2011 |

OTHER PUBLICATIONS

Templeton (World J. Surg. (2009) vol. 33, pp. 685-697).*
Rao, DD, et al., "Enhanced target gene knockdown by a bifunctional shRNA: a novel approach of RNA interference", Cancer Gene Therapy, 2010, 1-12.
Rao, DD, et al. "Systematic Identification of Bi-functional Short-Hairpin RNA ((bi-shRNA)) Specific for Single-Nucleotide KRAS Mutations", Molecular Therapy, May 16, 2012, 20:1::53-131.
Rao, DD, et al., "siRNA vs. shRNA: Similarities and Differences", Advanced Drug Delivery Reviews, Advanced Drug Delivery Reviews, 2009, 61:P746-759.
Rejiba, S., et al., "K-ras Oncogene Silencing Strategy Reduces Tumor Growth and Enhances Gemcitabine Chemotherapy Efficacy for Pancreatic Cancer Treatment", Cancer Science, Jul. 2007, 98:7:1128-1136.
Zhaohui, W., et al., "RNA Interference and Cancer Therapy", Pharmaceutical Research, 2011, 28: 2983-2995.
Brummelkamp, T., et al., "Stable suppression of tumorigenicity by virus-mediated RNA interference", Cancer Cell, Sep. 2002, 2:243-247.
de Ynigo-Mojado, L., et al., "Efficient Allele-Specific Targeting of LRRK2 R1441Mutations Mediated by RNAi", PloS One, Jun. 2011, 6(6):1-10.
Fleming, J.F., et al., "Molecular Consequences of Silencing Mutant K-ras in Pancreatic Cancer Cells: Justification for K-ras-Directed Therapy", Molecular Cancer Research, 2005, 3:413-423.
Geng, Chang-Ming, et a., "Design of Functional Small Interfering RNAs Targeting Amyotrophic Lateral Sclerosis-Associated Mutant Alleles", 2011, Chin Med J, 124(1):106-110.
Huang, H. et al., "Profiling of mismatch discrimination in RNAi enabled rational design of allele-specific siRNAs", Nucleic Acids Research, 2009, 37(22): 7560-7569.
Ohnishi, Y., et al., "Assessment of Allele-Specific Gene Silencing by RNA Interference with Mutant and Wild-Type Reporter Alleles", Journal of RNAi and Gene Silencing, 2006, 2(1):154-160.
Pfister, E.L., "Five siRNAs Targeting Three SNPs May Provide Therapy for Three-Quarters of Huntington's Disease Patients", Current Biology, May 12, 2009, 19:774-778.
Rao, D., et al., "Bifunctional Short Hairpin RNA (bi-shRNA): Design and Pathway to Clinical Application", Chapter 14, Abstract, Methods in Molecular Biology, 2013, 942:259-278.
Rao, D., et al., "Enhanced Target Gene Knockdown by a Bifunctional shRNA: A Novel Approach of RNA Interference", Cancer Gene Therapy, 2010, 1-2.
Schwarz, D.S., et al., "Designing siRNA That Distinguish Between Genes That Differ by a Single Nucleotide", PLoS Genetics, Sep. 2006, 2(9):1307-1318.
Sierant, M., et al., "Specific Silencing of L392V PSEN1 Mutant Allele by RNA Interference", International Journal of Alzheimer's Disease, vol. 2011, Article ID 809218, 1-14.
Smakman, N., et al., "Dual Effect of KrasD12 Knockdown on Tumorigenesis: Increased Immune-Mediated Tumor Clearance and Abrogation of Tumor Malignancy", Oncogene, 2005. 24:8338-8342.
Takahashi, M., et al., "Tailor-Made RNAi Knockdown Against Triplet Repeat Disease-Causing Alleles", PNAS, Dec. 14, 2010, 107(50):21731-21736.
Zhang, Z., et al., "Knockdown of Mutant K-ras Expression by Adenovirus-Mediated siRNA Inhibits the In Vitro and in Vivo Growth of Lung Cancer Cells", Cancer Biology & Therapy, Nov. 2006, 5(11):1481-1486.
Zhang, Y-A, et al., "Antitumor Activity of an Oncolytic Adenovirus-Delivered Oncogene Small Interfering RNA"., Cancer Research, 2006, 66:9736-9743.

\* cited by examiner

*Primary Examiner* — Jon E Angell
(74) *Attorney, Agent, or Firm* — Chalker Flores, LLP; Edwin S. Flores

(57) ABSTRACT

The present invention includes compositions and methods for making and using a bifunctional shRNAs capable of reducing an expression of a K-ras gene, e.g., a mutated K-ras gene, wherein at least one target site sequence of the bifunctional RNA molecule is located within the K-ras gene and wherein the bifunctional RNA molecule is capable of activating a cleavage-dependent and a cleavage-independent RNA-induced silencing complex for reducing the expression level of K-ras.

17 Claims, 7 Drawing Sheets

BI-FUNCTIONAL SHORT-HAIRPIN RNA (BI-SHRNA) SPECIFIC FOR SINGLE-NUCLEOTIDE *KRAS* MUTATIONS

CROSS-REFERENCE TO RELATED APPLICATIONS

This application claims priority to U.S. Provisional Application Ser. No. 61/644,875, filed May 9, 2012, the entire contents of which are incorporated herein by reference.

TECHNICAL FIELD OF THE INVENTION

The present invention relates in general to the field of cancer treatment, and more particularly, to a bi-functional shRNA that is specific for K-ras mutations.

STATEMENT OF FEDERALLY FUNDED RESEARCH

None.

REFERENCE TO A SEQUENCE LISTING

The present application includes a Sequence Listing which has been submitted in ASCII format via EFS-Web and is hereby incorporated by reference in its entirety. Said ASCII copy, created on May 7, 2013, is named GRAD:1025.txt and is 208 KB in size.

BACKGROUND OF THE INVENTION

Without limiting the scope of the invention, its background is described in connection with K-ras.

The KRAS (Kirsten-ras) oncogene is mutated in a significant proportion of pancreatic ductal adenocarcinoma (PDAC), colorectal and non-small-cell lung cancers (NSCLC). In the majority of PDAC (70-90%) patients carrying KRAS mutations, the five-year survival rate is less than 5%. KRAS is a member of guanine nucleotide-binding protein family and is an integral component of multiple intracellular signaling pathways including epidermal growth factor receptor (EGFR). The overwhelming majority of mutations in KRAS are single nucleotide somatic mutations resulting in single amino acid substitutions at codons 12 or 13. G12D, G12V, G12R and G12C KRAS mutations comprise >90% of KRAS mutations found in PADC patients. KRAS mutations essentially result in constitutively active KRAS and unregulated downstream signaling.

Targeted agents such as the antibody Cetuximab (in colorectal cancer) and the small molecular inhibitor vemurafenib (in BRAF mutant melanoma), perform poorly in patients with KRAS mutations. Consequently an effective cancer therapeutic strategy requires KRAS mutation selectivity sparing wild-type functionality. There remains a great need for compositions, methods and treatments for cancers with KRAS mutations.

SUMMARY OF THE INVENTION

In one embodiment, the present invention includes a bifunctional shRNAs capable of reducing an expression of a K-ras gene; wherein at least one target site sequence of the bifunctional RNA molecule is located within the K-ras gene, wherein the bifunctional RNA molecule is capable of activating a cleavage-dependent and a cleavage-independent RNA-induced silencing complex for reducing the expression level of K-ras. In one aspect, the bifunctional shRNA comprises at least one sequence defined by SEQ ID NOS: 1 to 22. In another aspect, the bifunctional shRNA comprises at least one sequence defined by SEQ ID NOS: 31 to 52, or 53 to 56. In another aspect, the at least one target site sequence is within a human K-ras gene cDNA sequence (SEQ ID NOS: 27 to 30). In another aspect, the K-ras is a mutated K-ras. In another aspect, the bifunctional shRNA comprise triplet inserts that target specific K-ras mutations selected from SEQ ID NO.: 2, 18, 20, 21, or a combination of SEQ ID NOS: 2, 18 and 20; or a combination of SEQ ID NOS: 21, 2 and 18.

In one embodiment, the present invention includes an expression vector comprising: a promoter; and a nucleic acid insert operably linked to the promoter, wherein the insert encodes one or more shRNA capable of inhibiting an expression of at least one target gene that is a K-ras gene via RNA interference; wherein the one or more shRNA comprise a bifunctional RNA molecule that activates a cleavage-dependent and a cleavage-independent RNA-induced silencing complex for reducing the expression level of K-ras. In one aspect, the target gene sequence comprises SEQ ID NO: 1 to 5. In another aspect, a sequence arrangement for the shRNA comprises a 5' stem arm-19 nucleotide target, which is K-ras-TA-15 nucleotide loop-19 nucleotide target complementary sequence-3' stem arm-Spacer-5' stem arm-19 nucleotide target variant-TA-15 nucleotide loop-19 nucleotide target complementary sequence-3' stem arm. In another aspect, the nucleic acid insert comprises at least one sequence selected from SEQ ID NO: 6 to 27. In another aspect, the at least one shRNA has a target site sequence that is within a mutated K-ras gene cDNA sequence. In another aspect, the present invention includes a therapeutic delivery system comprising: a therapeutic agent carrier; and an expression vector comprising a promoter and a nucleic acid insert operably linked to the promoter, the nucleic acid insert encoding one or more short hairpin RNA (shRNA) capable inhibiting an expression of a target gene sequence that is K-ras gene via RNA interference; wherein the one or more shRNA comprise a bifunctional RNA molecule that activates a cleavage-dependent and a cleavage-independent RNA-induced silencing complex for reducing the expression level of K-ras. In another aspect, the therapeutic agent carrier is a compacted DNA nanoparticle. In another aspect, the DNA nanoparticle is compacted with one or more polycations. In another aspect, the one or more polycations is a 10 kDA polyethylene glycol (PEG)-substituted cysteine-lysine 3-mer peptide (CK30PEG10k). In another aspect, the compacted DNA nanoparticles are further encapsulated in a liposome. In another aspect, the liposome is a bilamellar invaginated vesicle (BIV). In another aspect, the liposome is a reversibly masked liposome. In another aspect, the therapeutic agent carrier is a liposome. In another aspect, the target gene sequence comprises SEQ ID NOS: 27 to 30. In another aspect, the nucleic acid insert comprises at least one of the sequences selected from SEQ ID NOS: 31 to 52 or 53 to 56. In another aspect, the insert is selected from SEQ ID NOS: 1-22. In another aspect, the bifunctional shRNA comprise triplet inserts that target specific K-ras mutations selected from SEQ ID NO.: 2, 18, 20, 21, 55, or a combination of SEQ ID NOS: 2, 18 and 20; or a combination of SEQ ID NOS: 21, 2 and 18.

In one embodiment, the present invention includes a method to deliver one or more shRNAs to a target tissue expressing a K-ras gene comprising the steps of: preparing an expression vector comprising a promoter and a nucleic acid insert operably linked to the promoter that encodes the one or more shRNA, wherein the one or more shRNA comprise a bifunctional RNA molecule that activates a cleavage-dependent and a cleavage-independent RNA-induced silencing complex for reducing the expression level of K-ras; combining the expression vector with a therapeutic agent carrier, wherein the therapeutic agent carrier comprises a liposome; and administering a therapeutically effective amount of the expression vector and therapeutic agent carrier complex to a patient in need thereof. In one aspect, the therapeutic agent carrier is a compacted DNA nanoparticle. In another aspect, the DNA nanoparticle is compacted with one or more polycations, wherein the one or more polycations comprise a 10 kDA polyethylene glycol (PEG)-substituted cysteine-lysine 3-mer peptide (CK30PEG10k) or a 30-mer lysine condensing peptide. In another aspect, the compacted DNA nanoparticles are further encapsulated in a liposome, wherein the liposome is a bilamellar invaginated vesicle (BIV) and is decorated with one or more "smart" receptor targeting moieties. In another aspect, the one or more "smart" receptor targeting moieties are small molecule bivalent beta-turn mimics. In another aspect, the liposome is a reversibly masked liposome. In another aspect, the liposome is a bilamellar invaginated vesicle (BIV). In another aspect, the liposome is a reversibly masked liposome. In another aspect, the one or more "smart" receptor targeting moieties are small molecule bivalent beta-turn mimics. In another aspect, the nucleic acid insert comprises a sequence selected from SEQ ID NOS: 1 to 22 or 53 to 56. In another aspect, the bifunctional shRNA comprise triplet inserts that target specific K-ras mutations selected from SEQ ID NO.: 2, 18, 20, 21, or a combination of SEQ ID NOS: 2, 18 and 20; or a combination of SEQ ID NOS: 21, 2 and 18.

In one embodiment, the present invention includes a method to inhibit an expression of a K-ras gene in one or more target cells comprising the steps of: selecting the one or more target cells; and transfecting the target cell with a vector that expresses one or more short hairpin RNA (shRNAs) capable of inhibiting an expression of a K-ras gene in the one or more target cells via RNA interference, wherein the one or more shRNA comprise a bifunctional RNA molecule that activates a cleavage-dependent and a cleavage-independent RNA-induced silencing complex for reducing the expression level of K-ras. In another aspect, the shRNA incorporates siRNA (cleavage-dependent) and miRNA (cleavage-independent) motifs. In another aspect, the bifunctional shRNA comprise triplet inserts that target specific K-ras mutations selected from SEQ ID NO.: 2, 18, 20, 21, or a combination of SEQ ID NOS: 2, 18 and 20; or a combination of SEQ ID NOS:21, 2 and 18.

In one embodiment, the present invention includes a method of suppressing a tumor cell growth in a human subject comprising the steps of: identifying the human subject in need for suppression of the tumor cell growth; and administering an expression vector in a therapeutic agent carrier complex to the human subject in an amount sufficient to suppress the tumor cell growth, wherein the expression vector expresses one or more shRNA capable inhibiting an expression of a target gene that is K-ras in the one or more target cells via RNA interference; wherein the one or more shRNA comprise a bifunctional RNA molecule that activates a cleavage-dependent and a cleavage-independent RNA-induced silencing complex for reducing the expression level of the target gene; wherein the inhibition results in an apoptosis, an arrested proliferation, or a reduced invasiveness of the tumor cells. In another aspect, the therapeutic agent carrier comprises a bilamellar invaginated vesicle (BIV). In another aspect, the therapeutic agent carrier comprises one or more "smart" receptor targeting moieties are small molecule bivalent beta-turn mimics. In another aspect, the step of administering is selected from the group consisting of subcutaneous, intravenous, intraperitoneal, intramuscular, and intravenous injection. In another aspect, the step of administering comprises intratumoral injection. In another aspect, the step of administering comprises injecting with a DNA:lipoplex. In another aspect, the tumor cell growth expresses K-ras. In another aspect, the tumor cell growth is human pancreatic ductal adenocarcinoma. In another aspect, the tumor cell growth is selected from the group consisting of lung cancer, colon cancer, melanoma, insulinoma, mesothelioma, ovarian cancer, and pancreatic cancer. In another aspect, the tumor cell growth is a pancreatic cancer. In another aspect, the bishRNA is selected from SEQ ID NOS: 1 to 22 or 53 to 56. In another aspect, the bifunctional shRNA comprise triplet inserts that target specific K-ras mutations selected from SEQ ID NO.: 2, 18, 20, 21, or a combination of SEQ ID NOS: 2, 18 and 20; or a combination of SEQ ID NOS:21, 2 and 18. In another aspect, the method may further comprise a combination therapy with a second anti-neoplasmic agent. In another aspect, the method may further comprise a combination therapy with cetuximab or vemurafenib.

Another embodiment of the present invention includes an expression vector comprising 1, 2, 3, 4, 5, 6, 7, 8, 9, 10, 12, 13, 14, 15, 16, 17, 18, 20, 21, 25, 50, 75, or 100 bifunctional shRNAs inserts capable of reducing an expression of a mutant K-ras gene; wherein at least one target site sequence of the bifunctional RNA molecule is located within the K-ras gene, wherein the bifunctional RNA molecule is capable of activating a cleavage-dependent and a cleavage-independent RNA-induced silencing complex for reducing the expression level of K-ras. In one aspect, the bifunctional shRNA is selected from SEQ ID NOS: 1 to 22 or 53 to 56. In another aspect, the bifunctional shRNA comprise triplet inserts that target specific K-ras mutations selected from at least one of G12D-G12V-G12R, G12C-G12D-G12R, G12D-G12V-G12R, or G12C-G12D-G12R. In another aspect, the bifunctional shRNA comprise triplet inserts that target specific K-ras mutations selected from SEQ ID NO.: 2, 18, 20, 21, or a combination of SEQ ID NOS: 2, 18 and 20; or a combination of SEQ ID NOS:21, 2 and 18.

Another embodiment of the present invention includes a cell comprising an expression vector that includes 1, 2, 3, 4, 5, 6, 7, 8, 9, 10, 12, 13, 14, 15, 16, 17, 18, 20, 21, 25, 50, 75, or 100 bifunctional shRNAs inserts capable of reducing an expression of a mutant K-ras gene; wherein at least one target site sequence of the bifunctional RNA molecule is located within the K-ras gene, wherein the bifunctional RNA molecule is capable of activating a cleavage-dependent and a cleavage-independent RNA-induced silencing complex for reducing the expression level of K-ras. In one aspect, the bifunctional shRNA is selected from SEQ ID NOS: 1 to 22 or 53 to 56. In another aspect, the bifunctional shRNA increases the expression of non-mutated K-ras. In another aspect, the bifunctional shRNA comprise triplet inserts that target specific K-ras mutations selected from SEQ ID NO.: 2, 18, 20, 21, or a combination of SEQ ID NOS: 2, 18 and 20; or a combination of SEQ ID NOS:21, 2 and 18.

Another embodiment of the present invention includes a method of evaluating a candidate drug believed to be useful in treating cells or tissues that comprise at least one mutated K-ras, the method comprising: (a) measuring the level of expression of at least one of a wild-type K-ras and one or more mutated K-ras genes in the cells or tissues; (b) administering a candidate drug to a first subset of cells or tissues, and a placebo to a second subset of cells or tissues; (c) repeating step (a) after the administration of the candidate drug or the placebo; and (d) determining if the candidate drug reduces the expression of mutated K-ras as compared to wild-type K-ras that is statistically significant as compared to any reduction occurring in the second subset of cells or tissues, wherein a statistically significant reduction indicates that the candidate drug is useful in treating K-ras induced disease. In one aspect, the cells or tissue further express one or more detectable genes have modified to comprise a wild-type K-ras and one or more mutated K-ras, wherein the level of expression of the detectable label correlates with the effect of the candidate substance on the wild-type K-ras and one or more mutated K-ras. In another aspect, the cells or tissue have been modified to express a bifunctional shRNAs capable of reducing an expression of a K-ras gene, wherein at least one target site sequence of the bifunctional RNA molecule is located within the K-ras gene and wherein the bifunctional RNA molecule is capable of activating a cleavage-dependent and a cleavage-independent RNA-induced silencing complex for reducing the expression level of K-ras.

Another embodiment of the present invention includes a method of evaluating a candidate drug believed to be useful in treating cells or tissues that comprise at least one mutated K-ras that is effectively silenced, the method comprising: (a) measuring one or more of the following: a. the level of expression of at least a wild-type K-ras and one or more mutated K-ras genes in the cells or tissues; b. the level of expression of a candidate gene or a group of candidate genes in an cellular environment with the lowered expression of one or more mutated K-ras genes in the cancer cells or tissues; c. the effect of a candidate drug on the phenotype of such cells comprised of lowered expression of one or more mutated K-ras genes in the cancer cells or tissues; (b) administering a candidate drug to a first subset of said cells or tissues, and a placebo to a second subset of said cells or tissues; (c) repeating step (a) after the administration of the candidate drug or the placebo; and (d) determining if the candidate drug is effective in producing determined phenotype in an cellular environment with reduced expression of mutated K-ras as compared to K-ras mutant expressing cellular environment that is statistically significant as compared to any reduction occurring in the second subset of cells or tissues, wherein a statistically significant reduction indicates that the candidate drug is useful in treating disease without significant K-ras mutation background. In one aspect, the cells or tissue further express one or more detectable genes have modified to comprise a wild-type K-ras and one or more mutated K-ras, wherein the level of expression of the detectable label correlates with the effect of the candidate substance on the wild-type K-ras and one or more mutated K-ras. In another aspect, the cells or tissue have been modified to express a bifunctional shRNAs capable of reducing an expression of a K-ras gene, wherein at least one target site sequence of the bifunctional RNA molecule is located within the K-ras gene and wherein the bifunctional RNA molecule is capable of activating a cleavage-dependent and a cleavage-independent RNA-induced silencing complex for reducing the expression level of K-ras. In another aspect, the cells or tissue have been modified to express a bifunctional shRNA that comprises one or more inserts that target specific K-ras mutations selected from SEQ ID NO.: 2, 18, 20, 21, or a combination of SEQ ID NOS: 2, 18 and 20; or a combination of SEQ ID NOS: 21, 2 and 18.

BRIEF DESCRIPTION OF THE DRAWINGS

For a more complete understanding of the features and advantages of the present invention, reference is now made to the detailed description of the invention along with the accompanying figures and in which:

(FIG. 7A) PANC-1 cell transfected with G12D targeting constructs. (FIG. 7B) Compares G12D constructs on KRAS knockdown with 3 cell lines. (FIG. 7C) Compares G12C constructs on KRAS knockdown with 3 cell lines.

DETAILED DESCRIPTION OF THE INVENTION

Figure 1:
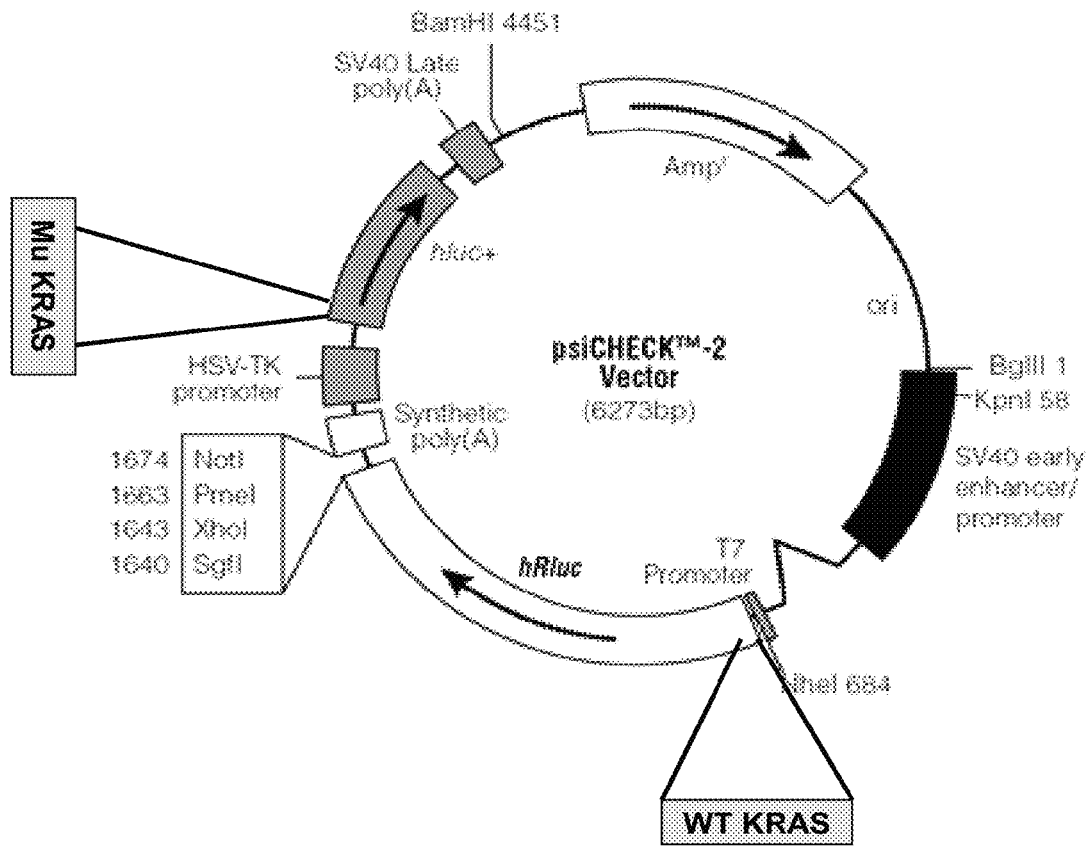
FIG. 1 shows one schematic of a test vector. The first 17 amino acids of wild-type KRAS were inserted into the amino-terminus of Renilla luciferase gene (hRluc) of the psiCHECK2 vector while the first 17 amino acids of G12D, G12V, G12R or G12C KRAS mutants were inserted into the amino-terminus of Firefly luciferase gene (hluc+) on the same vector.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The activating mutations in the ras proto-oncogenes family render them constitutively active are observed frequently in all human cancers. In particular, activating mutations in KRas are observed in greater than 90% of pancreatic cancers. Kras mutations are difficult to target specifically with small molecules, thus knocking down Kras mutations without affecting the wt Kras expression is a viable approach for the treatment of cancer. All RNAi based Kras mutation knockdown is either targeting at one specific mutation or concomitantly knockdown the wt expression. This invention discloses novel design and construct which is able to knockdown over 90% of identified Kras mutations in pancreatic cancer without drastically reduce the wt Kras expression.

RNAi is the Nobel-prize winning discovery by Fire and Mello in 1998, which has fostered an exponential number of studies and publications furthering the understanding of gene function and stimulating numerous phase I and II clinical trials. This naturally occurring gene-silencing mechanism by small RNAs, which includes endogenous microRNA (miRNA), is highly dependent on gene sequence; thus the mechanism can, in theory, be used to inhibit the expression of any targeted gene[s] with strong specificity. RNAi is not limited by the pharmacologic constraints inherent to the development of small molecules which creates an opportunity to access traditionally "undruggable" targets for disease treatment.

The central player of this mechanism is the RNA Induced Silencing Complex (RISC). The process starts with double-stranded small RNA (composed of a passenger strand and a guide strand) which is incorporated into the pre-RISC followed by the cleavage-dependent or cleavage-independent release of the passenger strand to form the guide strand containing RISC. The guide strand (anti-sense to mRNA) guides the RISC to recognize the target mRNA through sequence complementarity (full or extended partial). A key component of RISC is the family of Argonaute proteins (Ago), Ago 1, 2, 3 and 4 in mammalian systems, of which only Ago 2 has endonuclease activity so as to allow for cleavage of the target mRNA for further degradation (cleavage dependent pathway); all the Ago containing RISC can function through a cleavage-independent effector pathway resulting in translation repression and mRNA sequestration in p-body with subsequent degradation. The cleavage-dependent effector process requires extensive homology between guide strand and both the passenger strand and target mRNA, particularly in the central region; the cleavage-independent effector process, on the other hand, only requires partial homology between guide strand and both the passenger strand and target mRNA.

The present invention takes advantage of both cleavage dependent and cleavage independent loading at the RISC complex, not the events that are downstream from the RISC complex. Thus, as used herein the phrase "cleavage dependent and cleavage independent" refers to the design of RNA(s) that are specifically targeted to RISC and the cleavage dependent and cleavage independent activities at the RISC complex, i.e., loading. It has been found herein and in the parent application for this case, that these "bifunctional shRNAs" have a higher inhibitory activity than the sum of targeting each individual part of the RISC complex. Thus, the higher inhibitory activity of the present invention.

RNA interference can be triggered either by synthetic double stranded small interfering RNA (siRNA) or by vector driven short hairpin RNA (shRNA). Both siRNA and vector driven shRNA have been demonstrated to be effective in in vitro and in vivo applications, each with their respective advantages. Most siRNA are structurally designed to promote efficient incorporation into the Ago2 containing RISC, the RNase III containing Dicer-substrate design improves the efficiency of siRNA at least 10-fold by initial association and processing at the pre-RISC. Vector driven shRNA utilizes the host microRNA biogenesis pathway, which appears to be more efficient. siRNA is more readily chemically modified while shRNA expression can be modulated and regulated by specific promoters.

The present inventors developed the novel vector driven shRNA technology, the bi-functional shRNA (bi-shRNA), to further improve the efficiency of RNAi by harnessing both cleavage-dependent and cleavage-independent pathways of RISC loading in one pre-programed molecule. The vector driven bi-shRNA includes two stem-loop structures for each mRNA target sequence, one stem-loop shRNA has perfect complementarity at the stem and the second stem-loop shRNA contains mismatches on the passenger strand of the stem (thereby differing from prior art mismatched RNA that include the mismatch on the guide strand). Importantly, following incorporation into the RISC, the guide strands derived from each of the two structures are fully complementary to the mRNA target sequence but are associated with different Ago containing RISCs. The bi-shRNA design leads to more rapid onset of gene silencing, higher efficacy, and greater durability when compared with either siRNA or conventional shRNA. Currently personalized cancer therapy with target specific bi-shRNA is transitioned into the clinic in Phase I studies using a modified bilamellar invaginated liposome delivery vehicle. Key molecular methods involved in design, construction, and the implementation of bi-shRNA are provided below.

Depending on that objective and the embodiments, several different vectors, promoters, or plasmid backbones and delivery systems can be used. It has been found useful to choose an expression vector with efficient transgene expression. The present inventors recognized that an expression vector with powerful promoters, e.g., an extended CMV promoter containing IE 5'UTR and partial Intron A (pUMVC3), is more effective than those with a cloning site immediately adjacent to the CMV promoter. In certain embodiments it is beneficial to have a stretch of lead transcript before the stem-loop structures. In addition, if more than one vector usage is planned, an effective shuttle strategy should be worked out beforehand; modification by PCR amplification of the expressed cassette is not as efficient. The choice of promoter is also important; RNA polymerase III promoters are much stronger in expression but competitively saturate the endogenous miRNA maturation process at both the nuclear export and RISC loading steps resulting in lethal toxicity in vitro and in vivo with certain delivery vehicles. RNA polymerase II promoters, although less strong in expression, works efficiently and is much less toxic vis-á-vis competition for the endogenous miRNA pathway.

In certain embodiments a sequence that can act in more than one species is designed, particularly if multiple animal model systems are utilized. For most target genes, it is possible to find stretches of target nucleotides that are conserved between species. For finding a sequence that is both conserved and optimum for knockdown, one has to compare the homology-matched sequence with the selected target site sequence.

Public accessible computer programs using differing algorithms (e.g. Dharmacon RNAi design center (www.dharmacon.com) and IDT (www.idtdna.com) are readily available and can be used to locate appropriate target sites within the targeted gene. A search with most computer programs will often yield a preliminary first set of targets for further analysis. Some available publications offer do and do-not suggestions. A BLAST search for each target sequence is to be taken in order to analyze potential cross homology with other mRNAs within the species of interest.

Once the target site sequence is selected, the bi-shRNA design process can begin; the design process is presented below. The bi-shRNA stem-loop structure used by the inventors employs the well-analyzed miR-30a backbone, although, any functional miRNA backbone can be used. The bi-shRNA consists of the two stem-loop structures on a miR-30a backbone located immediately adjacent to each other with a gap about 10 nucleotides long. A longer nucleotide gap can be used and multiple units of bi-sh RNA can be designed to string together in a single transcript targeting either a single gene at multiple sites or multiple different genes simultaneously.

To construct the expression unit to be placed in the multiple cloning sites of an expression vector, an assembly strategy using synthetic oligonucleotides sequentially linked together has been developed. Alternatively, one can also outsource the synthesis of the gene construct with the specified sequence to a biotechnology service company. For the oligonucleotide assembly process, overlapping DNA fragments were designed and synthesized. Because of redundant sequences in the two stem-loop structures, it is necessary to initially ligate the 5' fragments and 3' fragments. The 5' fragment and the 3' fragment can then be purified on gel and further ligated to the middle linking fragments. This assembly process is efficient and, with careful design, many fragments can be repetitively used for different bi-functional constructs.

For each target, it is the best to design and construct at least three bi-functional constructs to compare and from which to select a construct with high knockdown efficiency for further evaluation. Knockdown efficiency can be compared in vitro in tissue culture cells. The present inventors recognized that is generally difficult to compare the knockdown efficiency with endogenously expressed genes because in vitro transfection methods have widely different efficiencies; this is particularly so when the transfection efficiency is low as the knockdown is hard to assess due to background noise from untransfected cells.

Efficacy and efficiency of target gene knockdown by bi-shRNA can be tested with a variety of in vitro and in vivo systems depending on the target and planned application. This in vitro assessment can be conducted following transfection of the bi-shRNA expression plasmids in a variety of cultured cells. The present inventors found that transfections by both electroporation and by liposome (e.g., Lipofectamine 2000) are highly effective, when the amount of plasmid DNA is carefully controlled using a control vector or universal random sequence. For Lipofectamine or a related agent, the present inventors found that the reverse transfection method, in general, is less toxic than the forward transfection method. Target gene knockdown can be assessed by either qRT-PCR for target gene mRNA or by Western and/or ELISA for target gene protein. In one assay methods the expression of mature shRNA by stem-loop RT-PCR is detected, in another essay method, the target mRNA cleavage is detected by 5' RNA-Ligand Mediated RACE (5' RLM-RACE). Stem-loop RT-PCR is a sensitive method dependent on the specific probe primer used; in addition, one can specifically detect and quantify both the passenger strand and guide strand. For bi-shRNA, the method can differentially score both the fully complementary as well as the mismatched (partially complementary) passenger strand. The 5' RLM-RACE method requires ligation of an RNA oligomer onto the cleaved mRNA end, consequently, the method is rendered less efficient. Insofar as a number of rounds of amplifications are often required, a nested primer design is essential to ensure specificity.

Evaluable functionality of bi-shRNA relies on effective plasmid delivery into target cells. The inventors recognize that some in vitro transfection systems often do not translate to inherently more complex in vivo animal models. There are numerous delivery systems designed specifically for systemic applications in vivo. The present inventorsutilize the fusogenic, cationic DOTAP:cholesterol bilamellar invaginated vesicle lipoplex (BIV) for in vivo studies and has successfully translated it to the clinic. Modification strategies for more focused biodistribution, targeted delivery, and enhanced intracellular uptake are developed. An effective lipoplex should use plasmids devoid of any contaminants from host E. coli. Although endo-free plasmid purification kit produced plasmids are generally used, GLP or GMP produced plasmids are more effective. Unfortunately, colanic acid and other non-endotoxin associated polysaccharides co-purify with DNA by anion exchange chromatography and by cesium chloride density gradient centrifugation. Therefore, endotoxin removal does not remove these contaminants, and HPLC cannot detect these contaminants. To correct this, the Superclean™ procedure has been developed to generate ultra-high quality plasmid DNA, cleansed of these contaminants, for in vivo and clinical applications. Liposome preparation involves highly specialized equipment; the present inventors routinely generate the DOTAP:cholesterol BIV in a GMP facility. Pre-made liposome may be obtained from a collaborator or purchased from a vendor. The process of preparing lipoplex with high quality liposome and plasmid DNA is described below. The lipoplex formulation can be achieved in most laboratory settings. Once the lipoplex is made, the formulation can be delivered systemically to experimental animals either through slow tail vein injection or with catheters. Target site vector expression can be analyzed using the PCR method for plasmid DNA and the stem-loop RT-PCR for mature bi-shRNA, respectively. bi-shRNA functionality can be assayed with the 5' RLM-RACE for target mRNA cleavage and with Western blot or IHC for target protein knockdown. These analyses can be performed at about 48 hours post treatment. For efficacy, repeated delivery into the experimental animal is often required; the dosing schedule needs to be experimentally determined and optimized.

The invention provides that target gene-specific shRNAs may be designed to enter into and interact with the cleavage-dependent RISC and cleavage-independent RISC pathways. As used herein, the term "bifunctional shRNA" generally means one or more RNA molecules, each of which include a double stranded sequence that resides within a stem portion of separate stem-loop structures, wherein a first RNA molecule is designed to be presented to a cleavage-dependent RISC pathway and a second RNA molecule is designed to be presented to a cleavage-independent RISC pathway. In certain embodiments, the bi-shRNA is all on a single strand.

More specifically, a first guide strand sequence is complementary, preferably 100% complementary, to at least a portion of an mRNA transcript encoded by a target gene. The invention provides that this guide strand (which is initially bonded to the passenger strand to form the double stranded stem) comprises a nucleic acid sequence that is capable of binding to the mRNA transcript of the target gene, and is presented to the cleavage-dependent RISC pathway. The invention provides that such binding of the guide strand sequence to the mRNA transcript, and presentation to the cleavage-dependent RISC pathway, causes degradation of the mRNA transcript.

In particular embodiments, it is provided that the second guide strand sequence is at least partially complementary to at least a portion of the mRNA transcript encoded by the target gene. More particularly, the second guide strand sequence may contain a first portion that is complementary, preferably 100% complementary, to the mRNA transcript encoded by the target gene, whereas a second portion of the guide strand sequence contains certain bases that are mismatched with the corresponding sequence of the target gene mRNA transcript.

As used herein, a "mismatched" base pair refers to two nitrogenous bases within a nucleic acid sequence that, when bound (or hybridized) to each other, do not follow Chargaffs rules of base pairing. Chargaffs rules provide that the purine adenine (A) within a first nucleic acid sequence will pair with the pyrimidine thymine (T) (or uridine (U)) within a second nucleic acid sequence. Furthermore, Chargaffs rules provide that the purine guanine (G) within a first nucleic acid sequence will pair with the pyrimidine cytosine (C) within a second nucleic acid sequence. Thus, a base pairing between two strands (nucleic acid sequences) that does not follow and comply with such rules would be deemed a "mismatched" base pair, e.g., a pairing between G and U, A and G, A and C, G and T, G and U, and so on. A guide strand within the double stranded sequence of the stem-loop structures shown therein, which contain one or more "mismatched" base pairs relative to the passenger strand, creates a bulge in the double stranded stem sequence.

As used herein the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., a-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "expression vector" as used herein in the specification and the claims includes nucleic acid molecules encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. The term "promoter" refers to any DNA sequence which, when associated with a structural gene in a host yeast cell, increases, for that structural gene, one or more of 1) transcription, 2) translation or 3) mRNA stability, compared to transcription, translation or mRNA stability (longer half-life of mRNA) in the absence of the promoter sequence, under appropriate growth conditions.

The term "oncogene" as used herein refers to genes that permit the formation and survival of malignant neoplastic cells (Bradshaw, T. K.: Mutagenesis 1, 91-97 (1986).

As used herein the term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

The term "hybridizing" refers to any process by which a strand of nucleic acid binds with a complementary strand through base pairing.

The term "transfection" refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein the term "bi-functional" refers to a shRNA having two mechanistic pathways of action, that of the siRNA and that of the miRNA. The term "traditional" shRNA refers to a DNA transcription derived RNA acting by the siRNA mechanism of action. The term "doublet" shRNA refers to two shRNAs, each acting against the expression of two different genes but in the "traditional" siRNA mode.

As used herein, the term "liposome" refers to a closed structure composed of lipid bilayers surrounding an internal aqueous space. The term "polycation" as used herein denotes a material having multiple cationic moieties, such as quaternary ammonium radicals, in the same molecule and includes the free bases as well as the pharmaceutically-acceptable salts thereof.

Accordingly, the bifunctional shRNAs may comprise shRNAs designed to enter into and interact with both cleavage-dependent RISC and cleavage-independent RISC. A higher level of gene "knock-down" is achieved using such bifunctional shRNAs compared to other currently-available RNAi methods and compositions, including siRNAs and conventional shRNAs (i.e., shRNA constructs designed to enter cleavage-dependent RISC or cleavage-independent RISC, but not both).

As used herein, gene "knock-down" refers to effective quantitative and durable inhibition of expression. Such gene "knock-down" may be manifested, and/or apparent, in the suppression of target gene mRNA translation, increased target cell apoptosis and/or cell kill.

As used herein, "target gene" refers to a nucleic acid sequence in a cell, wherein the expression of the sequence may be specifically and effectively modulated using the bifunctional shRNA. In certain embodiments, the target gene may be implicated in the growth (proliferation), maintenance (survival), and/or migratory (metastatic) behavior of an individual's cancer. The invention provides, however, that the target gene may be implicated in any other disease or medical condition, and is not limited to genes implicated in cancer. For example, the target gene may represent any sequence that an investigator or clinician wishes to silence (i.e., reduce the expression level of such target gene).

Vector sequence may comprise a promoter, which is operably linked (or connected), directly or indirectly, to a sequence encoding the bifunctional shRNAs. Such promoters may be selected based on the host cell and the effect sought. Non-limiting examples of suitable promoters include constitutive and inducible promoters, such as inducible RNA polymerase II (pol II)-based promoters. Non-limiting examples of suitable promoters further include the tetracycline inducible or repressible promoter, RNA polymerase I or III-based promoters, the pol II dependent viral promoters, such as the CMV-IE promoter, and the pol III U6 and H1 promoters. The bacteriophage T7 promoter may also be used (in which case it will be appreciated that the T7 polymerase must also be present). The invention shall not be restricted to the use of any single promoter, especially since the invention may comprise two or more bifunctional-shRNAs (i.e., a combination of effectors), including but not limited to incorporated shRNA singlets. Each incorporated promoter may control one, or any combination of, the shRNA singlet components.

In certain embodiments, the promoter may be preferentially active in the targeted cells, e.g., it may be desirable to preferentially express the bifunctional shRNA molecules in tumor cells using a tumor cell-specific promoter. Introduction of such constructs into host cells may be effected under conditions whereby the two or more RNA molecules that are contained within the bifunctional shRNA precursor transcript initially reside within a single primary transcript, such that the separate RNA molecules (each comprising its own stem-loop structure) are subsequently excised from such precursor transcript by an endogenous ribonuclease. The invention further provides that splice donor and acceptor sequences may be strategically placed within the primary transcript sequence to promote splicesome-mediated nuclear processing. The resulting mature shRNAs may then induce degradation, and/or translation repression, of target gene mRNA transcripts produced in the cell. Alternatively, each precursor stem-loop structure may be produced as part of a separate transcript, in which case each shRNA-encoding sequence will preferably include its own promoter and transcription terminator sequences. Additionally, the bifunctional shRNA precursor transcript may reside within a single primary transcript, which, optionally, further comprises of one or more mRNA sequences that encode one or more functional mammalian proteins. For example, the one or more mRNA sequences may encode certain proteins that are known to bolster a patient's immune system, or otherwise provide some preventative and/or therapeutic effect that will operate in parallel with the bifunctional shRNA.

The stem-loop structures of the shRNA molecules described herein may be about 40 to 100 nucleotides long or, preferably, about 50 to 75 nucleotides long. The stem region may be about 19-45 nucleotides in length (or more), or more preferably about 20-30 nucleotides in length. The stem may comprise a perfectly complementary duplex (but for any 3' tail), however, bulges or interior loops may be present, and even preferred, on either arm of the stem. The number of such bulges and asymmetric interior loops are preferably few in number (e.g., 1, 2 or 3) and are about 3 nucleotides or less in size. The terminal loop portion may comprise about 4 or more nucleotides, but preferably not more than about 25. More particularly, the loop portion will preferably be 6-15 nucleotides in size.

As described herein, the stem regions of the bifunctional shRNAs comprise passenger strands and guide strands, whereby the guide strands contain sequences complementary to the target mRNA transcript encoded by the target gene(s). Preferably, the G-C content and matching of guide strand and passenger strand is carefully designed for thermodynamically-favorable strand unwind activity with or without endonuclease cleavage. Furthermore, the specificity of the guide strand is preferably confirmed via a BLAST search (www.ncbi.nim.nih.qov/BLAST).

Expression level of multiple target genes may be modulated using the methods and bifunctional shRNAs described herein. For example, the invention provides that a first set of bifunctional shRNAs may be designed to include a sequence (a guide strand) that is designed to reduce the expression level of a first target gene, whereas a second set of bifunctional shRNAs may be designed to include a sequence (a guide strand) that is designed to reduce the expression level of a second target gene. The different sets of bifunctional shRNAs may be expressed and reside within the same, or separate, preliminary transcripts. In certain embodiments, such multiplex approach, i.e., the use of the bifunctional shRNAs described herein to modulate the expression level of two or more target genes, may have an enhanced therapeutic effect on a patient. For example, if a patient is provided with the bifunctional shRNAs described herein to treat, prevent, or ameliorate the effects of cancer, it may be desirable to provide the patient with two or more types of bifunctional shRNAs, which are designed to reduce the expression level of multiple genes that are implicated in the patient's cancer.

In certain embodiments, the invention further provides that the bifunctional shRNA sequences may comprise stem sequences of naturally occurring miRNAs (e.g., miR-30, *C. elegans* let-7 and/or lin-4). While the presence of a miR-30 loop, for example, may be desirable, the invention provides that variations of that structure may be tolerated, wherein loops may be used that are greater than 72%, preferably greater than 79%, more preferably greater than 86%, and most preferably, greater than 93% identical to, for example, the miR-30 sequence (determined using well-known computer programs such as the BESTFIT program (Wisconsin Sequence Analysis Package, Version 8 for Unix, Genetics Computer Group, University Research Park, 575 Science Drive, Madison, Wis. 53711)).

The precursor sequences (or constructs) encoding the bifunctional shRNAs may be introduced into host cells using any of a variety of techniques and delivery vehicles well-known in the art. For example, infection with a viral vector comprising one or more constructs may be carried out, wherein such viral vectors preferably include replication defective retroviral vectors, adenoviral vectors, adeno-associated vectors, lentiviral vectors, or measle vectors. In addition, transfection with a plasmid comprising one or more constructs may be employed. Such plasmids may be present as naked DNA, or may be present in association with, for example, a liposome (e.g., an immunoliposome). Still further, the delivery vehicle may consist of immunolipoplexes, targeted nanoparticles, targeted liposomes, cyclodextrins, nanoparticles, aptamers, dendrimers, chitosan, or pegylated derivatives thereof. The nature of the delivery vehicle may vary depending on the target host cell.

In-vivo delivery of the bifunctional shRNA-encoding constructs may be carried out using any one of a variety of techniques, depending on the target tissue. Delivery may be, for example, achieved by direct injection, inhalation, intravenous injection or other physical methods (including via micro-projectiles to target visible and accessible regions of tissue (e.g., with naked DNA). Administration may further be achieved via syringe needles, trocars, canulas, catheters, etc., as appropriate.

In addition to the methods of using the bifunctional shRNAs described herein, provided for are shRNAs themselves. Accordingly, additional aspects include nucleic acid sequences, which may comprise a single contiguous sequence or multiple distinct sequences that, individually or collectively, encode two or more RNA molecules. According to such embodiments, a first RNA molecule will comprise a double stranded sequence that includes a guide strand sequence that is complementary to a portion of an mRNA transcript encoded by a target gene, whereas a second RNA molecule comprises a second double stranded sequence that includes a second guide strand sequence that is partially complementary to a portion of such mRNA transcript. Preferably, the second guide strand sequence of the second RNA molecule comprises one or more bases that are mismatched with a nucleic acid sequence of the mRNA transcript encoded by the target gene. According to further aspects, expression vectors are provided which comprise the nucleic acid sequences, and may be used to carry out the methods, and express the bifunctional shRNAs, described herein.

Still further, methods of using the nucleic acid sequences and bifunctional shRNAs are described herein to prevent, treat and/or ameliorate the effects of one or more medical conditions, including without limitation various types of cancer. For example, the invention provides that the bifunctional shRNAs described herein may be used to reduce the expression level of one or more target genes that are implicated in cancer cell growth, survival, and/or metastasis. For example, as demonstrated in the Examples below, the bifunctional shRNAs may be used to reduce the expression level of certain target genes that encode scaffold proteins, which have been found to be over-expressed in cancer cells. Non-limiting examples of such target genes include K-ras.

RNA Interference: The introduction of artificial double-stranded small interfering RNAs (siRNAs) into animal and plant cells can induce the degradation of targeted mRNA molecules with complementary sequence; the process is known as RNA interference (RNAi) (Sharp 2001; Hutvagner and Zamore 2002; Zamore 2002) (see U.S. Pat. No. 6,506,559). RNAi has emerged as a useful experimental tool with strong potential for therapeutic applications (Fire, Xu et al. 1998; Hammond, Bernstein et al. 2000; Elbashir, Harborth et al. 2001; Senzer, Rao et al. 2009; Wang Z 2011). However, in mammalian cells, induction of RNAi using shRNAs requires the transfection of RNA oligonucleotides, which can be inefficient with the duration of effective silencing limited by vehicle disassembly time and siRNA biologic half life. Despite these limitations, in a recent early results publication of a clinical phase I study, Davis and colleagues have convincingly demonstrated target specific silencing and site-specific cleavage with systemic delivery of a pegylated, transferrin decorated, cyclodextrin-based siRNA targeting the M2 subunit of ribonucleotide reductase (RRM2) (CALAA-01) (Davis, Zuckerman et al. 2010). Three reported patients with biopsy accessible melanoma, who were treated as per the dose-escalation Phase I study, received 18, 24, or 30 mg/m2 CALAA-01 by intravenous infusion on days 1, 3, 8, and 10 of a 21 day cycle. Voluntary biopsies were performed after the final dose of cycle 1 in each and compared to archived tumor, and at 1 month post cycle 1 (prior to initiation of cycle 2) and on the day of the final dose of cycle 2 in the patient treated at 30 mg/m2. RRM2 mRNA reduction was confirmed by qRT-PCR comparing post- and pre-cycle 2 tissue samples at 30 mg/m2. In the same patient, immunohistochemistry and Western blot pre- and post-cycle 1 showed a five-fold reduction in MMR2 protein. Supporting the proposed mechanism of action, 5'-RLM-RACE (5'-RNA-ligase-mediated rapid amplification of complementary DNA ends) confirmed the predicted cleavage site. This first-in-human demonstration of targeted tumor cell entry (using transmission electron microscopy) and mRNA and protein expression reduction along with predicted site-specific siRNA cleavage following systemic delivery brings added impetus to translational application of RNAi.

siRNA requires chemical modification to increase serum stability, cellular uptake and duration of action. Alternatively, siRNA can be constructed as a short hairpin RNA (shRNA). shRNA consists of a stem-loop structure that can be transcribed in cells from RNA polymerase III (or, less frequently used, RNA polymerase II) promoter on a plasmid construct (Miyagishi and Taira 2002; Yu, DeRuiter et al. 2002). Constitutive expression of shRNA from a plasmid independently from the chromosome provides an advantage over synthetic siRNA. The shRNA expression units can be incorporated into a variety of plasmids and viral vectors for intracellular delivery and nuclear import. In addition, vector based shRNA expression can also be regulated or induced (Gossen and Bujard 1992; Gupta, Schoer et al. 2004; Dickins, Hemann et al. 2005). shRNAs, as opposed to synthetic siRNAs, are synthesized in the nucleus of cells, then processed and transported to the cytoplasm to be incorporated into the RNA-induced silencing complex (RISC) for activity (Cullen 2005). To be effective, shRNA has to be designed to utilize the endogenous cellular microRNA biogenesis machinery.

Bifunctional shRNA: As described above, RNA interference (RNAi) is a natural cellular regulatory process capable of inhibiting transcriptional, post-transcriptional and translational mechanisms thereby modulating gene expression. Using a miR30-scaffold, the present inventors developed a "bifunctional" RNAi strategy which demonstrated more effective silencing of target gene expression by concurrently inducing translational repression, and [GW 182-mediated] sequestration in the p-body (as a holding reservoir or promoting decapping, deadenylation and mRNA degradation) (cleavage-independent) as well as post-transcriptional mRNA mRNA cleavage (cleavage dependent) (Rao D 2010).

The present inventors have developed a novel bifunctional shRNA (bi-shRNAi) RNA interference (RNAi) technology. Bi-shRNAi allows for programmed endonuclease and non-endonuclease Argonaute (Ago) containing RISC(RNA-induced silencing complexes) loading to simultaneously effect mRNA cleavage, degradation, and translational repression resulting in higher potency and over longer duration than other RNAi mediators. In order to explore the potential of bi-shRNAi in KRAS mutant selective knockdown, an in vitro dual luciferase reporter assay system was established to systematically compare knockdown activity of the mutant allele and the wild-type allele in the same assay environment. The present invention includes the development of therapeutic agents specific for G12D, G12V, G12R and G12C for the treatment of, e.g., pancreatic ductal adenocarcinoma (PDAC).

Of a series of bi-shRNA expression vector constructs targeting G12D with a single nucleotide mutation at each position of the guide strand, it was found that the most discriminating knockdown activity for the mutant allele produced by placing a mutant nucleotide at position 2-4. By examining the knockdown effect of additional mismatches at other positions of the guide strand it was determined that the process was sequence-specific. Similar constructs were made for G12V, G12R and G12C mutations and they are effective in the knockdown of their respective target mutant alleles. G12R specific constructs cross-react with G12C mutants.

The constructs of the present invention were compared to control vector on KRAS knockdown using HEK-293 cells (wt/wt), PANC-1 cells (wt/G12D allele) and MiaPaCa2 cells (wt/G12C allele). G12D and G12C selective bi-shRNA expression vectors did not reduce KRAS expression in HEK-293 in contrast to reduction of KRAS expression in PANC-1 cell and MiaPaCa2 cell, respectively. It was found that, e.g., a single expression construct with multimeric bi-shRNA units capable of knocking down G12D, G12V, G12R and G12C is going to be tested for effectiveness and specificity in vitro and in vivo.

KRAS (Kirsten-ras) oncogene is mutated in a significant proportion of pancreatic ductal adenocarcinoma (PDAC), colorectal and non-small-cell lung cancers (NSCLC) (Downward J, Nat Rev Cancer. 2003; 3:11-22.). In the majority of PDAC (70-90%) patients carrying KRAS mutations, the five year survival rate is less than 5% (Saif M W et al. World J. Gastroenterol. 2007; 13; 4423-4430). KRAS is a member of guanine nucleotide-binding protein family and is an integral component of multiple intracellular signaling pathways including epidermal growth factor receptor (EGFR). The overwhelming majority of mutations in KRAS are single nucleotide somatic mutations resulting in single amino acid substitutions at codons 12 or 13. G12D, G12V, G12R and G12C KRAS mutations comprise >90% of KRAS mutations found in PADC patients (COSMIC Database, www.sanger.ac.uk/genetics/CGP/cosmic/). KRAS mutations essentially result in constitutively active KRAS and unregulated downstream signaling (Schubert S, et al. Nat Rev Cancer. 2007; 7: 295-308). In addition, targeted agents such as the antibody Cetuximab (in colorectal cancer) and the small molecular inhibitor vemurafenib (in BRAF mutant melanoma), perform poorly in patients with KRAS mutations (Karapetis C S, et al. N Engl J Med 2008; 259 (17): 1757-1765). Consequently an effective cancer therapeutic strategy requires KRAS mutation selectivity sparing wild-type functionality. The present inventors have recently developed a novel bi-functional shRNA RNA interference (bi-shRNAi) technology. Bi-shRNAi allows for programmed endonuclease and non-endonuclease Argonaute protein (Ago) containing RISC(RNA-induced silencing complexes) loading to simultaneously effect mRNA cleavage, degradation, and translational repression resulting in higher potency and over longer duration than other RNAi mediators. In order to explore the potential of bi-shRNAi in KRAS mutant selective knockdown, an in vitro dual luciferase reporter assay system was established to systematically compare knockdown activity of the mutant allele and the wild-type allele in the same assay environment. The goal of this project is to develop single therapeutic agent specifically targeting G12D, G12V, G12R and G12C mutant alleles for the treatment of PDAC.

siRNA distinguish between genes that differ by single nucleotide for allelic-specific knockdown has been systematically analyzed (Ref 1-4). Mutant allele specific knockdown has been demonstrated in vitro with model system for diseases such as Alzheimer's disease, Huntington's and Parkinson's disease (Ref. 10-13). Allelic specific gene silencing on KRAS mutations has been reported for single G12C, G12D or G 12V KRAS mutation (Ref. 5-9). No attempt was reported in achieving multiple KRAS mutant knockdown with a single agent. The present invention include a systematic approach to discover the most effective bi-shRNAi knockdown combinations for the four key KRAS mutants of PDAC.

(SEQ ID NO: 1) G12D, position 2. With underline are miR-30a backbone sequences.

<u>TCGACTGCTGTTGAAGTGAGCGCC</u>TGTGGTAGTTGGAGCTGAT<u>TAGTGA

AGCCACAGATGTA</u>ATCAGCTCCAACTACCACA<u>GTTGCCTACTGCCTCGG

AAGCAGCTCACTACATTACTCAGCTGTTGAAGTGAGCGCC</u>TGTGGTAGG

AAGAGATGAT<u>TAGTGAAGCCACAGATGTA</u>ATCAGCTCCAACTACCAC<u>AG

TTGCCTACTGCCTCGGAAGCTTAATAAAGGATCTTTTATTTTCATTGGC</u>

(SEQ ID NO: 2) G12D, position 3. With underline are miR-30a backbone sequences.

<u>TCGACTGCTGTTGAAGTGAGCGCC</u>GTGGTAGTTGGAGCTGATG<u>TAGTGA

AGCCACAGATGTA</u>CATCAGCTCCAACTACCAC<u>GTTGCCTACTGCCTCGG

AAGCAGCTCACTACATTACTCAGCTGTTGAAGTGAGCGCC</u>GTGGTAGTC

TTAGCTAATG<u>TAGTGAAGCCACAGATGTA</u>CATCAGCTCCAACTACCAC<u>G

TTGCCTACTGCCTCGGAAGCTTAATAAAGGATCTTTTATTTTCATTGGC</u>

(SEQ ID NO: 3) G12D, position 4. With underline are miR-30a backbone sequences.

<u>TCGACTGCTGTTGAAGTGAGCGCC</u>TGGTAGTTGGAGCTGATGG<u>TAGTGA

AGCCACAGATGTA</u>CCATCAGCTCCAACTACCA<u>GTTGCCTACTGCCTCGG

AAGCAGCTCACTACATTACTCAGCTGTTGAAGTGAGCGCC</u>TGGTAGTTA

CTGCTAATGG<u>TAGTGAAGCCACAGATGTA</u>CCATCAGCTCCAACTACC<u>AG

TTGCCTACTGCCTCGGAAGCTTAATAAAGGATCTTTTATTTTCATTGGC</u>

(SEQ ID NO: 4) G12D, position 5. With underline are miR-30a backbone sequences.

<u>TCGACTGCTGTTGAAGTGAGCGCC</u>GGTAGTTGGAGCTGATGGC<u>TAGTGA

AGCCACAGATGTA</u>GCCATCAGCTCCAACTACCC<u>GTTGCCTACTGCCTCGG

AAGCAGCTCACTACATTACTCAGCTGTTGAAGTGAGCGCC</u>GGTAGTTGT

CTCTGATAGC<u>TAGTGAAGCCACAGATGTA</u>GCCATCAGCTCCAACTACC<u>G

TTGCCTACTGCCTCGGAAGCTTAATAAAGGATCTTTTATTTTCATTGGC</u>

(SEQ ID NO: 5) G12D, position 6. With underline are miR-30a backbone sequences.

TCGACTGCTGTTGAAGTGAGCGCCGTAGTTGGAGCTGATGGCG**TAGTGA
AGCCACAGATGTACGCCATCAGCTCCAACTACGTTGCCTACTGCCTCGG
AAGCAGCTCACTACATTACTCAGCTGTTGAAGTGAGCGCC**GTAGTTGGA
GCTGATGGCGTAGTGAAGCCACAGATGTACGCCATCAGCTCCAACTACG
TTGCCTACTGCCTCGGAAGCTTAATAAAGGATCTTTTATTTTCATTGGC

(SEQ ID NO: 6) G12D, position 7. With underline are miR-30a backbone sequences.

TCGACTGCTGTTGAAGTGAGCGCCTAGTTGGAGCTGATGGCGT**TAGTGA
AGCCACAGATGTAACGCCATCAGCTCCAACTAGTTGCCTACTGCCTCGG
AAGCAGCTCACTACATTACTCAGCTGTTGAAGTGAGCGCC**TAGTTGGAT
GAGATGACGTTAGTGAAGCCACAGATGTAACGCCATCAGCTCCAACTAG
TTGCCTACTGCCTCGGAAGCTTAATAAAGGATCTTTTATTTTCATTGGC

(SEQ ID NO: 7) G12D, position 8. With underline are miR-30a backbone sequences.

TCGACTGCTGTTGAAGTGAGCGCCAGTTGGAGCTGATGGCGTA**TAGTGA
AGCCACAGATGTATACGCCATCAGCTCCAACTGTTGCCTACTGCCTCGG
AAGCAGCTCACTACATTACTCAGCTGTTGAAGTGAGCGCC**AGTTGGAGA
CTATGGAGTATAGTGAAGCCACAGATGTATACGCCATCAGCTCCAACTG
TTGCCTACTGCCTCGGAAGCTTAATAAAGGATCTTTTATTTTCATTGGC

(SEQ ID NO: 8) G12D, position 9.

TCGACTGCTGTTGAAGTGAGCGCCGTTGGAGCTGATGGCGTAGTAGTGA
AGCCACAGATGTACTACGCCATCAGCTCCAACGTTGCCTACTGCCTCGG
AAGCAGCTCACTACATTACTCAGCTGTTGAAGTGAGCGCCGTTGAAGCA
CGTGGTGTAGTAGTGAAGCCACAGATGTACTACGCCATCAGCTCCAACG
TTGCCTACTGCCTCGGAAGCTTAATAAAGGATCTTTTATTTTCATTGGC (SEQ ID NO: 9) G12D, position 10.

TCGACTGCTGTTGAAGTGAGCGCCTTGGAGCTGATGGCGTAGGTAGTGA
AGCCACAGATGTACCTACGCCATCAGCTCCAAGTTGCCTACTGCCTCGG
AAGCAGCTCACTACATTACTCAGCTGTTGAAGTGAGCGCCTTGGAGCTA
TAGGTCTAGGTAGTGAAGCCACAGATGTACCTACGCCATCAGCTCCAAG
TTGCCTACTGCCTCGGAAGCTTAATAAAGGATCTTTTATTTTCATTGGC (SEQ ID NO: 10) G12D, position 11.

TCGACTGCTGTTGAAGTGAGCGCCTGGAGCTGATGGCGTAGGCTAGTGA
AGCCACAGATGTAGCCTACGCCATCAGCTCCAGTTGCCTACTGCCTCGG
AAGCAGCTCACTACATTACTCAGCTGTTGAAGTGAGCGCCTGGAGCTGT
ATGCGTTCGCTAGTGAAGCCACAGATGTAGCCTACGCCATCAGCTCCAG
TTGCCTACTGCCTCGGAAGCTTAATAAAGGATCTTTTATTTTCATTGGC (SEQ ID NO: 11) G12D, position 9, mod 4.

TCGACTGCTGTTGAAGTGAGCGCCGTTGGAGCTGATGGCGTAGTAGTGA
AGCCACAGATGTACTATGCCATCAGCTCCAACGTTGCCTACTGCCTCGG
AAGCAGCTCACTACATTACTCAGCTGTTGAAGTGAGCGCCGTTGAAGCA
CGTGGTGTAGTAGTGAAGCCACAGATGTACTATGCCATCAGCTCCAACG
TTGCCTACTGCCTCGGAAGCTTAATAAAGGATCTTTTATTTTCATTGGC (SEQ ID NO: 12) G12D, position 10, mod 5.

TCGACTGCTGTTGAAGTGAGCGCCTTGGAGCTGATGGCGTAGGTAGTGA
AGCCACAGATGTACCTATGCCATCAGCTCCAAGTTGCCTACTGCCTCGG
AAGCAGCTCACTACATTACTCAGCTGTTGAAGTGAGCGCCTTGGAGCTA
TAGGTCTAGGTAGTGAAGCCACAGATGTACCTATGCCATCAGCTCCAAG
TTGCCTACTGCCTCGGAAGCTTAATAAAGGATCTTTTATTTTCATTGGC (SEQ ID NO: 13) G12D, POSITION 11, MOD 6.

TCGACTGCTGTTGAAGTGAGCGCCTGGAGCTGATGGCGTAGGCTAGTGA
AGCCACAGATGTAGCCTATGCCATCAGCTCCAGTTGCCTACTGCCTCGG
AAGCAGCTCACTACATTACTCAGCTGTTGAAGTGAGCGCCTGGAGCTGT
ATGCGTTCGCTAGTGAAGCCACAGATGTAGCCTATGCCATCAGCTCCAG
TTGCCTACTGCCTCGGAAGCTTAATAAAGGATCTTTTATTTTCATTGGC (SEQ ID NO: 14) G12D, POSITION 9, MOD 10.

TCGACTGCTGTTGAAGTGAGCGCCGTTGGAGCTCATGGCGTAGTAGT
GAAGCCACAGATGTACTACGCCATGAGCTCCAACGTTGCCTACTGCC
TCGGAAGCAGCTCACTACATTACTCAGCTGTTGAAGTGAGCGCCGTT
GAAGCACGTGGTGTAGTAGTGAAGCCACAGATGTACTACGCCATGAG
CTCCAACGTTGCCTACTGCCTCGGAAGCTTAATAAAGGATCTTTTAT
TTTCATTGGC (SEQ ID NO: 15) G12D, position 10, mod 11.

TCGACTGCTGTTGAAGTGAGCGCCttggagctCAtggcgtaggTAGTG
AAGCCACAGATGTACCTACGCCATGAGCTCCAAGTTGCCTACTGCCTC
GGAAGCAGCTCACTACATTACTCAGCTGTTGAAGTGAGCGCCttggag
ctATAggTCtaggTAGTGAAGCCACAGATGTACCTACGCCATGAGCTC
CAAGTTGCCTACTGCCTCGGAAGCTTAATAAAGGATCTTTTATTTTCA
TTGGC (SEQ ID NO: 16) G12D, position 11, mod 12.

TCGACTGCTGTTGAAGTGAGCGCCTGGAGCTCATGGCGTAGGCTAGT
GAAGCCACAGATGTAGCCTACGCCATGAGCTCCAGTTGCCTACTGCC

```
TCGGAAGCAGCTCACTACATTACTCAGCTGTTGAAGTGAGCGCCTGG

AGCTGTATGCGTTCGCTAGTGAAGCCACAGATGTAGCCTACGCCATG

AGCTCCAGTTGCCTACTGCCTCGGAAGCTTAATAAAGGATCTTTTAT

TTTCATTGGC
```

(SEQ ID NO: 17) G12V, position 3.

```
TCGACTGCTGTTGAAGTGAGCGCCGTGGTAGTTGGAGCTGTTGTAGT

GAAGCCACAGATGTACAACAGCTCCAACTACCACGTTGCCTACTGCC

TCGGAAGCAGCTCACTACATTACTCAGCTGTTGAAGTGAGCGCCGTG

GTAGTCTTAGCTATTGTAGTGAAGCCACAGATGTACAACAGCTCCAA

CTACCACGTTGCCTACTGCCTCGGAAGCTTAATAAAGGATCTTTTAT

TTTCATTGGC
```

(SEQ ID NO: 18) G12V, position 4.

```
TCGACTGCTGTTGAAGTGAGCGCCTGGTAGTTGGAGCTGTTGGTAGT

GAAGCCACAGATGTACCAACAGCTCCAACTACCAGTTGCCTACTGCC

TCGGAAGCAGCTCACTACATTACTCAGCTGTTGAAGTGAGCGCCTGG

TAGTTACTGCTATTGGTAGTGAAGCCACAGATGTACCAACAGCTCCA

ACTACCAGTTGCCTACTGCCTCGGAAGCTTAATAAAGGATCTTTTAT

TTTCATTGGC
```

(SEQ ID NO: 19) G12R, position 3.

```
TCGACTGCTGTTGAAGTGAGCGCCTGTGGTAGTTGGAGCTCGTTAGT

GAAGCCACAGATGTAACGAGCTCCAACTACCACAGTTGCCTACTGCC

TCGGAAGCAGCTCACTACATTACTCAGCTGTTGAAGTGAGCGCCTGT

GGTAGACTGAGCTAGTTAGTGAAGCCACAGATGTAACGAGCTCCAAC

TACCACAGTTGCCTACTGCCTCGGAAGCTTAATAAAGGATCTTTTAT

TTTCATTGGC
```

(SEQ ID NO: 20) G12R, position 4.

```
TCGACTGCTGTTGAAGTGAGCGCCGTGGTAGTTGGAGCTCGTGTAGT

GAAGCCACAGATGTACACGAGCTCCAACTACCACGTTGCCTACTGCC

TCGGAAGCAGCTCACTACATTACTCAGCTGTTGAAGTGAGCGCCGTG

GTAGTACTAGCTAGTGTAGTGAAGCCACAGATGTACACGAGCTCCAA

CTACCACGTTGCCTACTGCCTCGGAAGCTTAATAAAGGATCTTTTAT

TTTCATTGGC
```

(SEQ ID NO: 21) G12C, position 3.

```
TCGACTGCTGTTGAAGTGAGCGCCTGTGGTAGTTGGAGCTTGTTAGT

GAAGCCACAGATGTAACAAGCTCCAACTACCACAGTTGCCTACTGCC

TCGGAAGCAGCTCACTACATTACTCAGCTGTTGAAGTGAGCGCCTGT

GGTAGACTGAGCTAGTTAGTGAAGCCACAGATGTAACAAGCTCCAAC

TACCACAGTTGCCTACTGCCTCGGAAGCTTAATAAAGGATCTTTTAT

TTTCATTGGC
```

(SEQ ID NO: 22) G12C, position 4.

```
TCGACTGCTGTTGAAGTGAGCGCCGTGGTAGTTGGAGCTTGTGTAGT

GAAGCCACAGATGTACACAAGCTCCAACTACCACGTTGCCTACTGCC

TCGGAAGCAGCTCACTACATTACTCAGCTGTTGAAGTGAGCGCCGTG

GTAGTCTTAGCTTATGTAGTGAAGCCACAGATGTACACAAGCTCCAA

CTACCACGTTGCCTACTGCCTCGGAAGCTTAATAAAGGATCTTTTAT

TTTCATTGGC
```

Schematic of the Test Vectors. The first 17 amino acids of wild-type KRAS were inserted into the amino-terminus of Renilla luciferase gene (hRluc) of the psiCHECK2 vector while the first 17 amino acids of G12D, G12V, G12R or G12C KRAS mutants were inserted into the amino-terminus of Firefly luciferase gene (hluc+) on the same vector.

Insertion of KRAS Sequences into Renilla gene or Firefly gene: First 17 amino acids of human KRAS wild-type sequences: ATGACTGAATATAAACTTGTGGTAGTTG-GAGCTGGTGGCGTAGGCAAGAGT (SEQ ID NO:58) were inserted in Renilla gene sequences of psiCHECK2 at the translation initiation ATG. The nucleotide sequences in the region after the insertion of KRAS (WT) sequences are as follows (underlined are KRAS sequences):

```
                                        (SEQ ID NO: 23)
GCTAGCCACCATGACTGAATATAAACTTGTGGTAGTTGGAGCTGGT

GGCGTAGGCAAGAGTGCTTCCAAGGTGTACGACCCCGAGCAACGCA

AACGCATGATCACTGGGCCTCAGTGGTGGGCTCGCTGCAAGCAAAT

GAACGTGCTGGACTCCTTCATCAACTACTATGATTCCGAGAAGCAC

GCCGAGGAGGCACGTCGTGCCTCA
```

Briefly, the nomenclature is as follows: italics are renilla or firefly coding sequences, bold underlined in blacks are inserted KRAS sequence, bold are triplet codon for G12 and G13 and double underlines are restriction sites used for sub-cloning, except it appears black for Renilla.

First 17 amino acids of human KRAS mutant sequence (G12D):
ATGACTGAATATAAACTTGTGGTAGTTG-GAGCTGATGGCGTAGGCAAGAGT (SEQ ID NO:24) was inserted in Firefly gene sequences of psiCHECK2 at the translation initiation ATG. The nucleotide sequences in the region after the insertion of KRAS (mutant) sequences are as follows (underlined are KRAS sequences):

```
                                        (SEQ ID NO: 25)
CACTTCGCATATTAAGGTGACGCGTGTGGCCTCGAACACCGAGCGA

CCCTGCAGCGACCCGCTTAAAAGCTTGGCATTCCGGTACTGTTGGT

AAAGCCACCATGACTGAATATAAACTTGTGGTAGTTGGAGCTGATG

GCGTAGGCAAGAGTGCCGATGCTAAGAACATTAAGAAGGGCCCTGC

TCCCTTCTACCCTCTGGAGGATGG
```

Construction of Test Vectors: The DNA fragments with appropriate insertion were generated with gene synthesis process. Synthetic DNA fragments were inserted into psiCHECK2 to generate test vectors as listed below. Gene synthesis and vector construction were made under contract by Epoch Life Sciences Inc. (Missouri City, Tex.).

(pGBI70) psiCHECK2-KRAS-WT (GGTGGC): Digest the composite of KRAS(WT) in hRluc with NheI and DraIII and insert into NheI and DraIII sites of psiCHECK2 to form psiCHECK2-KRAS-WT (pGBI71) psiCHECK2-KRAS-WT/G12D (GATGGC): Digest the composite of KRAS(G12D) in hluc+ with MluI and PspOMI and insert into MluI and PspOMI sites of psiCHECK2-KRAS-WT to form psiCHECk2-KRAS-WT/G12D (pGBI72) psiCHECK2-KRAS-WT/G12V (GTTGGC): Digest the composite of KRAS(G12D) in hluc+ with MluI and PspOMI and insert into MluI and PspOMI sites of psiCHECK2-KRAS-WT to form psiCHECK2-KRAS-WT/G12V (pGBI73) psiCHECK2-KRAS-WT/G12R(CGTGGC): Digest the composite of KRAS(G12D) in hluc+ with MluI and PspOMI and insert into MluI and PspOMI sites of psiCHECK2-KRAS-WT to form psiCHECK2-KRAS-WT/G12R (pGBI74) psiCHECK2-KRAS-WT/G12C (TGTGGC): Digest the composite of KRAS(G12D) in hluc+ with MluI and PspOMI and insert into MluI and PspOMI sites of psiCHECK2-KRAS-WT to form psiCHECK2-KRAS-WT/G12C bi-shRNAi design and construction. Bi-shRNA design was accomplished essentially as published previously (Ref 14-15). Each bi-shRNA expression unit was put together via gene synthesis and inserted into the Sal I and Not I sites of the multiple cloning sites of pUMVC3 vector.

Cell transfection. Transfection of cells was performed either by electroporation (Gene Pulser MX Cell, BIO-RAD) or by Lipofectamine LTX (Invitrogen). Electroporation condition for HEK-293 cells essentially follows the pre-set condition stored in the instrument by the manufacturer. Transfection with Lipofectamine LTX follows the suggestion recommended by the manufacturer and further optimized by modulating input DNA concentration and Lipofectamine ratio. Reverse transfection method was used for all Lipofectamine transfection. Most co-transfections were performed with the optimized total concentration of DNA and Lipofectamine ratio with test vector and bi-shRNAi vector at 1 to 1 ratio. The test vector to b-shRNAi vector ratio was tested and optimized as well.

Dual-luciferase assay: Dual-luciferase assay were performed using Dual-Glo Luciferase Assay System (Promega) and essentially follow the instruction provided by the manufacturer. The luminescence measurement was carried out in 96 well format with Luminoskan Ascent Microplate Luminometer (Thermo Scientific). Essentially, cells were transfected in 96 well plates or plated in 96 well plate post transfection. Transfected cells were assayed either at 24 hrs or 48 hrs post transfection.

Cell growth inhibition assay: Cell growth inhibition assay were carried out either with Cell Titer-Blue Cell Viability Assay Reagent or Cell Titer-Glo Luminescent Cell Viability Assay Reagent (Promega) by following the manufacturer's recommended procedure. Each cell lines used were first optimized in assay development time.

KRAS knockdown assessed by western immunoblot: Cells were lysed with lysis buffer CelLytic-M (Sigma) and scraped off the surface of the culture dish, incubated at room temperature for 30 minutes on a slow shaker, and briefly centrifuged. A small aliquot for protein concentration estimation by Coomassie Bradford Plus Assay was taken with BSA as standard. The SoftMaxPro software was used to calculate the values and plot the standard curve. Equal amounts of protein (usually 5-20 ug) were separated on a pre-assembled 15% polyacrylamide gel electrophoresis (PAGE) using Mini-Protein II Cell system (Bio-Rad). Following electrophoresis, the separated proteins were electro-transferred on to a PVDF membrane with standard condition. Transferred membranes were first blocked with blocking buffer containing 5% non-fat dried milk in DPBS-T overnight at 4° C. After two changes of wash buffer, proteins were tagged first with determined dilution of primary antibody (for KRAS and β-Actin, Santa Cruz Biotechnology) and then with HRP-conjugated secondary antibody. Chemiluminescent detection was done by ECL Plus Western Blotting Detection reagents with G:BOX Chemi XT16 automated chemiluminescence image analyzer (Syngene, Frederick, Md.). Membranes can be stripped and re-probed with a different antibody or house keeping protein such as β-Actin.

Figure 2:
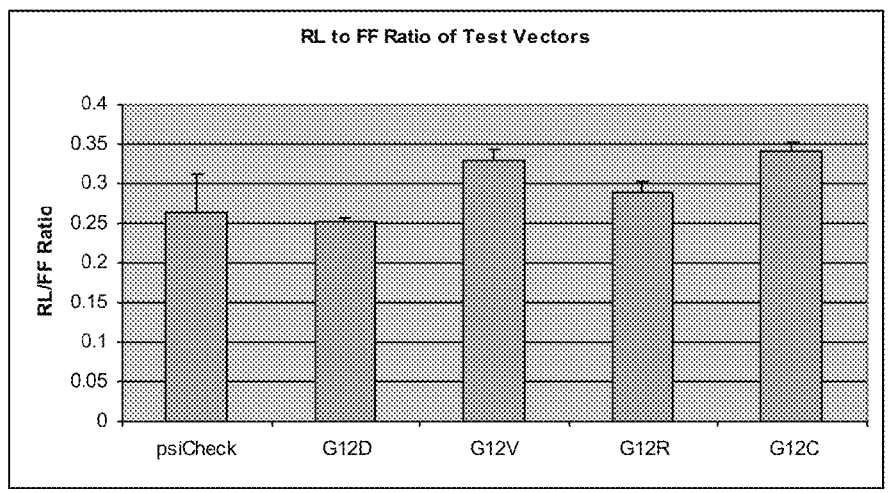
FIG. 2 shows the effect of wild-type and mutant expression of test vectors. Wild-type (Wt) and mutant (Mu) expression of each test vectors was compared to the parent psiCHECK2 vector using Dual-Glo Luciferase Assay System (Promega). The Wt to Mu expression comparison was assessed by the expression ratio of Renilla (RL) to Firefly (FF).

Test Vectors for Each Mutant Allele Retain the *Renilla* to Firefly Expression Ratio. The focus was to design allele specific knockdown bi-shRNA targeting four KRAS mutations that is most prevalent in PDAC. Four test vectors were constructed to test G12D, G12V, G12R or G12C mutant alleles individually. Each test vector construct was examined to ensure the insertion of KRAS sequences did not differentially affected the expression or activity of either *Renilla* (RL) or Firefly (FF) luciferase. Test vectors for G12D, G12V, G12R and G12C mutations all retained the similar RL to FF ratio as the parent psiCHECK2 vector (FIG. 2). The vector with only KRAS wt sequences inserted into RL luciferase (pGBI70) show reduced RL to FF ratio indicating the insertion affected RL luciferase activity (Data not shown), the RL to FF ratio were retained in mutant containing test vectors indicate the insertion of KRAS mutant sequences into FF luciferase affected FF activity similarly as RL.

FIG. 1 shows a schematic of the Test Vectors. The first 17 amino acids of wild-type KRAS were inserted into the amino-terminus of *Renilla* luciferase gene (hRluc) of the psiCHECK2 vector while the first 17 amino acids of G12D, G12V, G12R or G12C KRAS mutants were inserted into the amino-terminus of Firefly luciferase gene (hluc+) on the same vector.

It was found that test vectors for each mutant retain the *Renilla* to firefly expression ratio. FIG. 2 shows wild-type and mutant expression of test vectors. Wild-type (Wt) and mutant (Mu) expression of each test vectors was compared to the parent psiCHECK2 vector using Dual-Glo Luciferase Assay System (Promega). The Wt to Mu expression comparison was assessed by the expression ratio of *Renilla* (RL) to Firefly (FF).

Figure 3A:
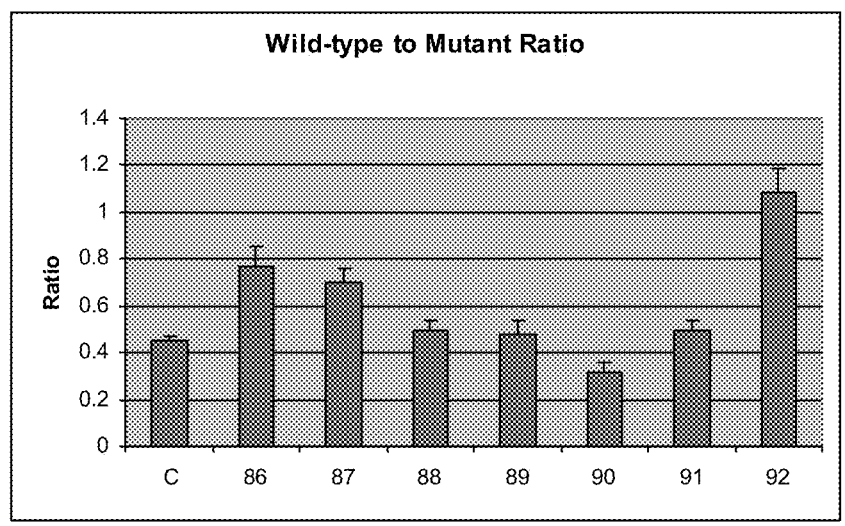
FIGS. 3A to 3C are a demonstration of an assay system of the present invention. By co-transfecting a test vector with bi-functional shRNA (bi-shRNA) expression vectors (86, 87, 88, 89, 90, 91 or 92, SEQ ID NOS.: 1 to 7, respectively), the preferential knockdown of mutant vs. wild-type (FIG. 3A) can be quickly assessed by FF to RL ratio (Panel a). Knockdown of mutant or wild-type can be further analyzed individually by compare RLU of FF (FIG. 3B) or RL (FIG. 3C) with empty vector control (C).
Figure 3B:
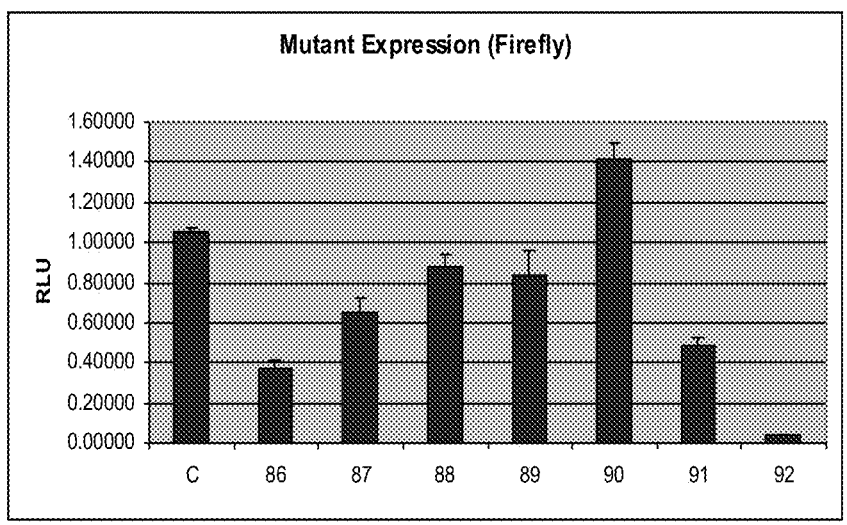
Figure 3C:
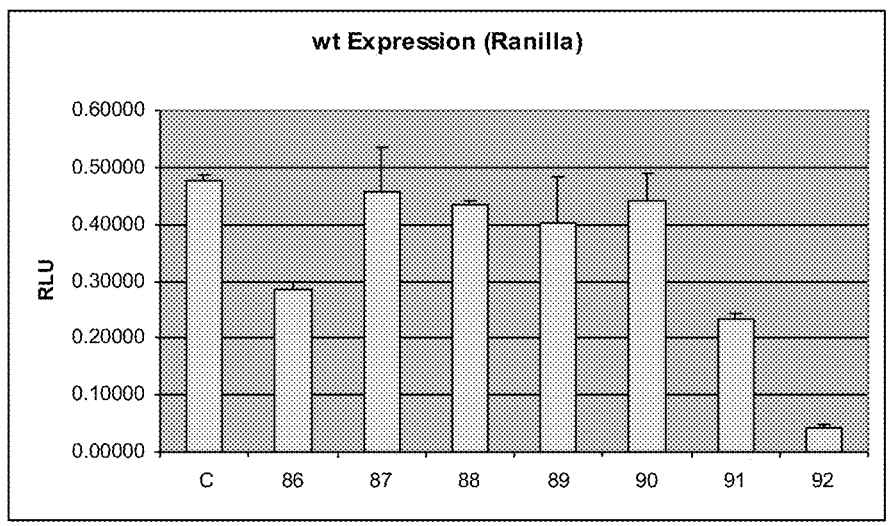

To test the assay system, several bishRNA expression constructs were constructed targeting G12D mutation and performed the co-transfection experiment with the test vector containing wt (RL) sequences and G12D mutant (FF) sequences. Seven bishRNA constructs were tested, each constructs has the complement of mutant allele sequence at various positions of the guide strand. Each bishRNA constructs were co-tranfected with the G12D test vector and the dual-luciferase assay were done at 48 hrs post-transfection. The collected data can be analyzed either by wild-type to mutant ratio as exemplified on FIG. 3*a*, or by relative luminescence unit (RLU) of Firefly (FIG. 3*b*) or *Renilla* (FIG. 3*c*). The microplate luminometer samples luminescence signals from a small area in each well without multiplying amplification factors. The triplicates of data usually have very small standard deviation and experiments are reproducible from experiment to experiment. The wild-type to mutant ratio provides a quick look at each bishRNA constructs in mutant versus wild-type knockdown. Wild-type to mutant ratio above the empty vector control (FIG. 3a, lane c) indicate advantage for mutant knockdown while equal or below the control indicate no advantage. Knockdown efficiency of either wild-type or mutant allele by each construct can also be compared to empty vector control. Each bishRNA constructs shows different characteristics in terms of wild-type or mutant knockdown efficiencies.

It was found that comparative knockdown efficiency on mutant versus WT can be assessed by Relative Luminescence Units (RLU) or *Renilla* (RL) to Firefly (FF) Ratio. FIG. 3: Demonstration of the Assay System. By co-transfecting a test vector with bi-functional shRNA (bi-shRNA) expression vectors (86, 87, 88, 89, 90, 91 or 92), the preferential knockdown of mutant vs. wild-type can be quickly assessed by FF to RL ratio (Panel a). Knockdown of mutant or wild-type can be further analyzed individually by compare RLU of FF (Panel b) or RL (Panel c) with empty vector control (C).

Next, a comparative knockdown efficiency was determined and it was found that efficiency varies when placing mutant sequence at various positions of the guide strand of bi-shRNA Constructs. Each bishRNA constructs show different characteristics in wild-type and mutant allele knockdown as shown on FIG. 3. Other publications have shown the central regions are important for allelic-specificity of siRNA mediated RNAi. To test and to understand the specificity of our bifunctional strategy, a series of constructs were made placing the complement of G12D mutated nucleotide at position 2 to 11 of the guide strand and systematically analyze the specificity and efficacy of each constructs. Position 2 to 11 encompassed both the seed region and the central region. Placing mutated nucleotide at position 5 and 10 (FIG. 4, P5 and P10) showed no knockdown of neither wild-type or mutant, on the other hand position 7, 8, 9 and 11 (FIG. 4, P7, P8, P9 and P11) are highly effective in both wild-type and mutant knockdown. Positions 2, 3 and 4 (FIG. 4, P2, P3 and P4) at the seed region showed the best discrimination in wild-type and mutant knockdown. Thus, seed region particularly positions 3 and 4 are the most effective in specificity of knockdown.

Figure 4:
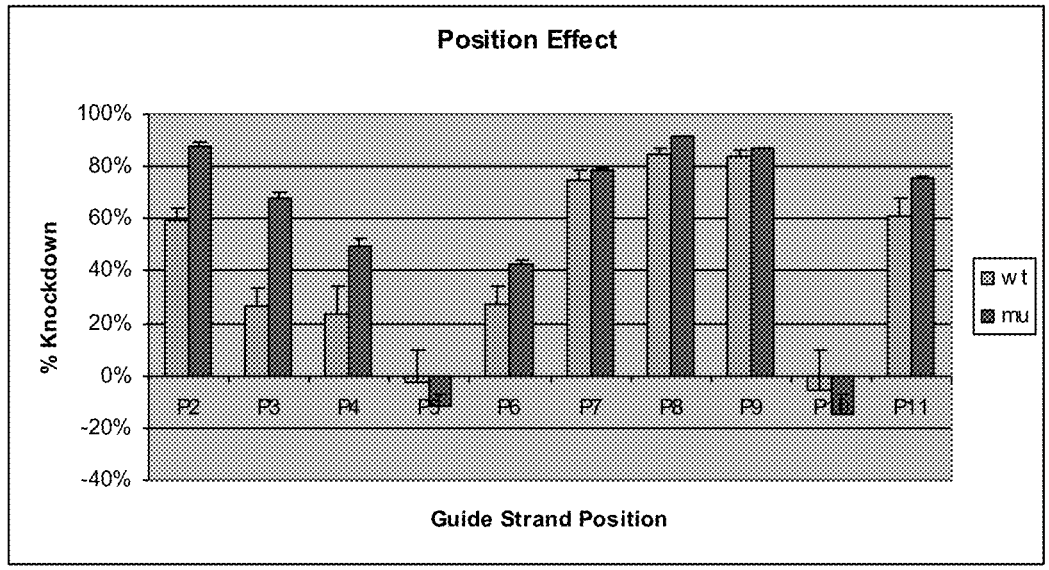
FIG. 4 shows the position effect for various mutants. Bi-shRNA constructs specific for G12D mutant were compared by placing the single mutated nucleotide sequence at one of the first 11 positions of the guide strand. Percentage knockdown for wild-type (wt) and for mutant (mu) was assessed for each construct. (n=3).

FIG. 4 shows the position effect of the bifunctional shRNAs of the present invention. Bi-shRNA constructs specific for G12D mutant were compared by placing the single mutated nucleotide sequence at one of the first 11 positions of the guide strand. Percentage knockdown for wild-type (wt) and for mutant (mu) was assessed for each construct. (n=3)

Additional mismatches were introduced into the guide strand. It was found that introducing additional mismatches at the guide strand significantly reduced the knockdown efficiency. Ohnishi and co-workers reported introducing mismatches at the seed region enhances mutant-allele recognition at the central region (1). bishRNA constructs with additional seed region mismatch were made for the central region constructs (mutated nucleotide at P9, P10 and P11 of the guide strand). bishRNA constructs were also made with mismatch juxtaposition to the mutated nucleotide to test the potential of knockdown two mutant allele with one construct. Co-transfection data with G12D test vector show seed region mismatch reduced both wild-type and mutant knockdown efficiency (FIG. 5, lane P9+P4 vs. lane P9; lane p10+p5 vs. p10; lane p11+p6 vs. p11) with only slight improvement on mutant recognition enhancement. Introducing mismatch juxtaposition to mutated nucleotide dramatically reduced the knockdown efficiency both for mutant and for wild type (FIG. 5, lane P9+P10 vs. lane P9; lane P10+P11 vs. lane P10; lane P11+P12 vs. lane P11).

Figure 5:
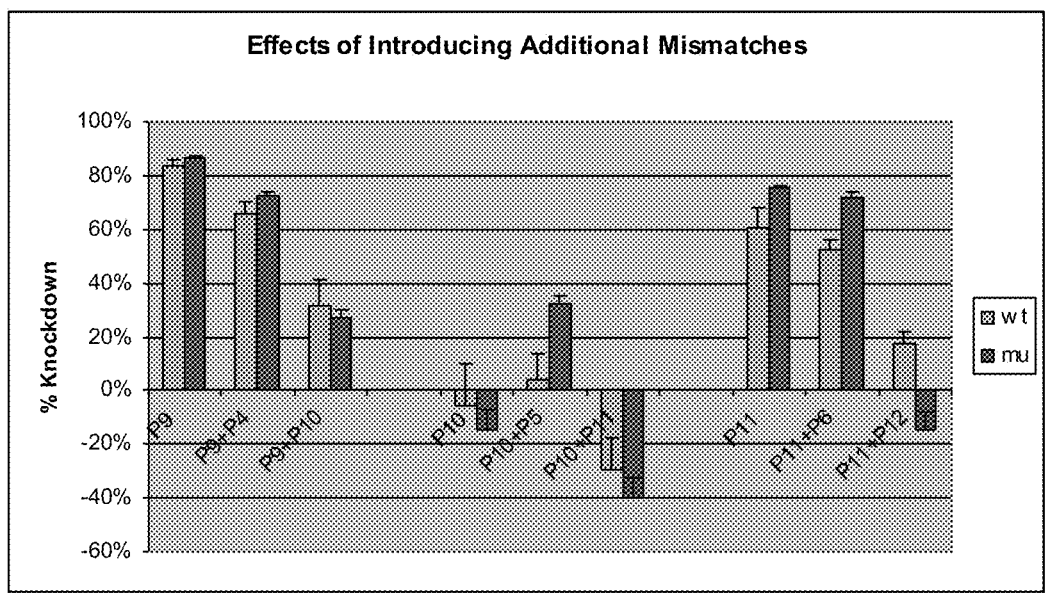
FIG. 5 shows a comparison when certain mismatches are introduced that reduced knockdown efficiency. G12D constructs with mutated nucleotide at the central region (p9, p10 and p11) were compared to constructs with additional mismatch either at the seed region or at juxtaposition to the mutated nucleotide: wild-type (wt) and for mutant (mu). (n=3).

FIG. 5 demonstrates the effect of introducing mismatches on knockdown efficiency. Ohnishi and co-workers reported introducing mismatches at the seed region enhances mutant recognition at the central region (1). G12D constructs with mutated nucleotide at the central region (p9, p10 and p11) were compared to constructs with additional mismatch either at the seed region or at juxtaposition to the mutated nucleotide: wild-type (wt) and mutant (mu). (n=3)

Figure 6:
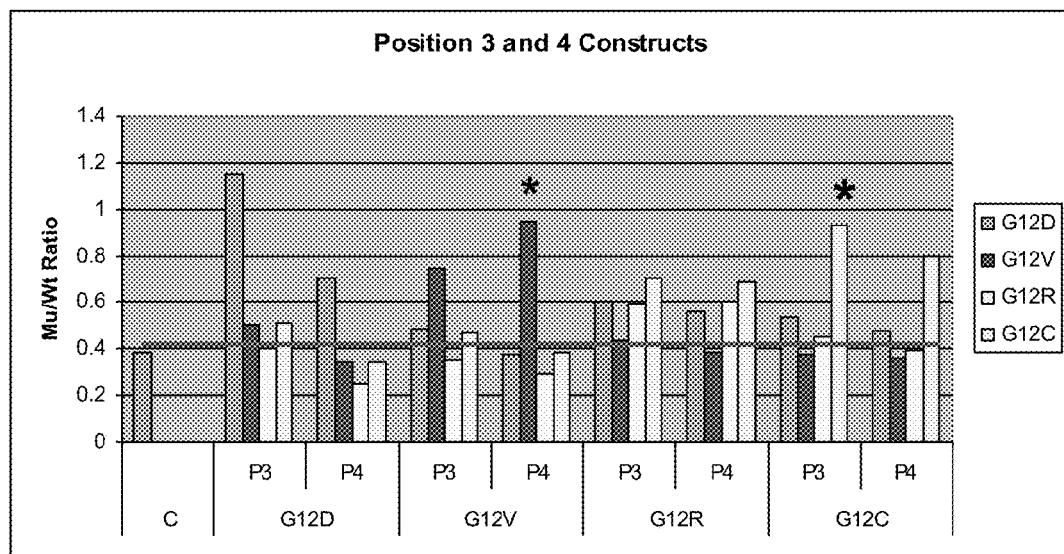
FIG. 6 show the selective knockdown on position 3 or 4 of constructs for G12D, G12V, G12R and G12C. Advantage of mutant knockdown was compared for all position 3 or 4 bi-shRNAi constructs for G12D, G12V, G12R and G12C against all test vectors specific for each of four mutants. The mutant to wild-type ratio above the empty vector control sample (sample C, the bar across) indicate strong knockdown advantage on specific mutant allele.

To broaden the possible effect and targeting of the bifunctional shRNA, an shRNA was targeted to a specific position of the target such that overlapping effects may be possible. It was found that constructs with mutated nucleotide at Either Position 3 or 4 is also selective for G12V, G12R and G12C. Constructs with mutated nucleotide at either position 3 or 4 for G12V, G12R and G12C mutations were tested along with G12D constructs against all four test vectors. Position 3 construct for G12D is more effective than position 4 construct (FIG. 6, G12D lanes) with little or no activity towards other mutants (FIG. 6, G12D lanes). Position 4 construct for G12V, on the other had, is more effective than position 3 construct (FIG. 6, G12V lanes) and has little or no activity towards other mutants (FIG. 6, G12V lanes). G12R constructs are not as selective, with slight better activity on mutant towards G12D, G12R and G12C rather evenly (FIG. 6, G12R lanes). For G12C, position 3 is better than position 4 with little or no activity towards other mutants (FIG. 6, G12C lanes). The knockdown efficiencies for wild-type or mutant for each constructs are summarized on table 1.

FIG. 6 demonstrates the selective knockdown on Position 3 or 4 Constructs for G12D, G12V, G12R and G12C. Advantage of mutant knockdown was compared for all position 3 or 4 bi-shRNAi constructs for G12D, G12V, G12R and G12C against all test vectors specific for each of four mutants. The mutant to wild-type ratio above the empty vector control sample (sample C, the bar across) indicate strong knockdown advantage on specific mutant allele.

Table 1 shows the wild-type and mutant allele knockdown efficiency of key bi-shRNA constructs. Table 1 summarize target sequences, guide strand sequence for key bi-shRNA constructs and each respective knockdown efficiency on mutant or wild-type alleles, SEQ ID NO.: 26-52, respectively.

Table 1 is a Summary of Position Effect on Knockdown SEQ ID NO.: 26-52.

| SEQ ID NO.: | Target Sequence | |
|---|---|---|
| 26 | C T T G T G G T A G T T G G A G C T G G T G G C G T A G G C A A G A G T | wt |
| 27 | C T T G T G G T A G T T G G A G C T G *A* T G G C G T A G G C | G12D |
| 28 | C T T G T G G T A G T T G G A G C T G *T* T G G C G T A G G C | G12V |
| 29 | C T T G T G G T A G T T G G A G C T *C* G T G G C G T A G G C | G12R |
| 30 | C T T G T G G T A G T T G G A G C T *T* G T G G C G T A G G C | G12C |

-continued

| | Guide Strand Sequence | KD Wt | KD Mu | |
|---|---|---|---|---|
| 31 | A C A C C A T C A A C C T C G A C T A | 59% | 88% | G12D pos 2 |
| 32 | C A C C A T C A A C C T C G A C T A C | 26% | 68% | G12D pos 3 |
| 33 | A C C A T C A A C C T C G A C T A C C | 23% | 50% | G12D pos 4 |
| 34 | C C A T C A A C C T C G A C T A C C G | -2% | -5% | G12D pos 5 |
| 35 | C A T C A A C C T C G A C T A C C G C | 27% | 43% | G12D pos 6 |
| 36 | A T C A A C C T C G A C T A C C G C A | 75% | 79% | G12D pos 7 |
| 37 | T C A A C C T C G A C T A C C G C A T | 84% | 92% | G12D pos 8 |
| 38 | C A A C C T C G A C T A C C G C A T C | 84% | 87% | G12D pos 9 |
| 39 | A A C C T C G A C T A C C G C A T C C | -6% | -8% | G12D pos 10 |
| 40 | A C C T C G A C T A C C G C A T C C G | 61% | 76% | G12D pos 11 |
| 41 | C A A C C T C G A C T A C C G T A T C | 65% | 72% | G12D pos 9 mod 4 |
| 42 | A A C C T C G A C T A C C G T A T C C | 4% | 32% | G12D pos 10 mod 5 |
| 43 | A C C T C G A C T A C C G T A T C C G | 52% | 72% | G12D pos 11 mod 6 |
| 44 | C A A C C T C G A G T A C C G C A T C | 32% | 27% | G12D pos 9 mod 10 |
| 45 | A A C C T C G A G T A C C G C A T C C | -10% | -7% | G12D pos 10 mod 11 |
| 46 | A C C T C G A G T A C C G C A T C C G | 17% | -8% | G12D pos 11 mod 12 |
| 47 | C A C C A T C A A C C T C G A C A A C | 16% | 84% | G12V pos 3 |
| 48 | A C C A T C A A C C T C G A C A A C C | 22% | 79% | G12V pos 4 |
| 49 | A C A C C A T C A A C C T C G A G C A | 14% | 55% | G12R pos 3 |
| 50 | C A C C A T C A A C C T C G A G C A C | 44% | 80% | G12R pos 4 |
| 51 | A C A C C A T C A A C C T C G A A C A | 25% | 77% | G12C pos 3 |
| 52 | C A C C A T C A A C C T C G A A C A C | 28% | 71% | G12C pos 4 |

Figure 7A:
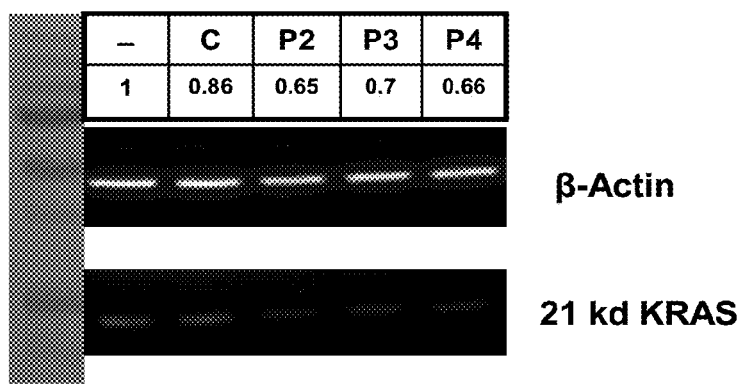
FIGS. 7A to 7C show Western immunoblot analysis of KRAS expression in bi-shRNA transfected Cells. HEK-293 (WT), PANC-1 (G12D allele) and MiaPaCa (G12C allele) were transfected with various mutant targeting bi-shRNA constructs. Cell extracts harvested 48 hrs post-transfection were analyzed semi-quantitatively with Western immunoblots.
Figure 7B:
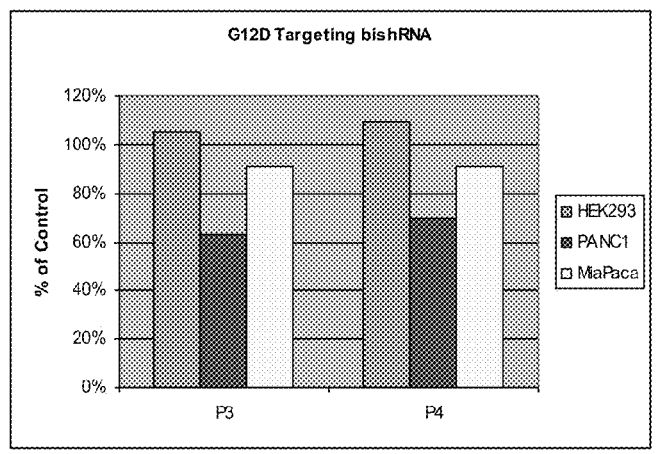

Next, the constructs were tested for effectiveness is cancer cells. Test constructs with KRAS wild-type cell line and pancreatic cancer cell lines with mutant alleles were tested. There is no antibody available to differentially recognize mutant KRAS protein versus wild-type KRAS protein, three different cell lines were used with three different genotypes to test differential knockdown of each constructs. HEK-293 is human embryonic kidney cell line with wild-type KRAS (KRAS+/+), PANC1 is human pancreatic cancer cell line with heterozygotic KRAS (KRAS+/G12D) and MiaPaCa2 is human pancreatic cancer cell line with heterozygotic KRAS (KRAS+/G12C). Positions 2, 3 and 4 constructs were able to knockdown KRAS expression with varied efficiency (FIG. 7A). Knockdown is rather not efficient, 65 to 70% of untransfected control may due to transfection efficiency and the presence of wild-type KRAS. Knockdown efficiency was further compared for position 3 and/or 4 constructs for K12D and K12C mutants with three different cell lines. G12D constructs did not appear to knockdown KRAS in HEK293 cells (FIG. 7B), most effective in knockdown KRAS in PANC 1 cells (FIG. 7B) and low KRAS knockdown activity in MiaPaCa2 cells (FIG. 7B). On the other hand, G12C constructs were not effective in KRAS knockdown both in HEK293 cells (FIG. 7C) and PANC1 cells (FIG. 7C), but effective in KRAS knockdown in MiaPaCa2 cells (FIG. 7C).

Figure 7C:
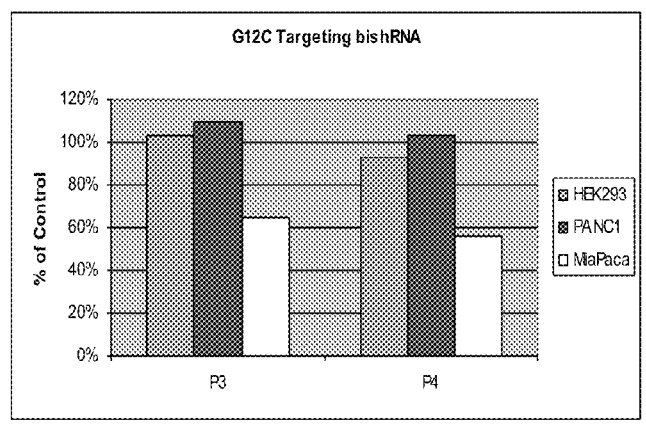

FIGS. 7A to 7C show a Western immunoblot analysis of KRAS expression in bi-shRNA transfected cells. HEK-293 (WT), PANC-1 (G12D allele) and MiaPaCa (G12C allele) were transfected with various mutant targeting bi-shRNA constructs. Cell extracts harvested 48 hrs post-transfection were analyzed semi-quantitatively with Western immunoblots. (a) PANC-1 cell transfected with G12D targeting constructs. FIG. 7B compares G12D constructs on KRAS knockdown with 3 cell lines. FIG. 7C compares G12C constructs on KRAS knockdown with 3 cell lines.

Table 2 summarizes the dose requirement between standard antisense, standard siRNA, standard shRNA and the bi-functional-shRNA of the present invention.

| Technology | Delivery | MTD | Effective Dose |
|---|---|---|---|
| Antisense | none | 3-4 mg/kg | ~3 mg/kg? |
| siRNA | Liposome | 0.336-1.0 mg/kg | 0.3->0.7 mg/kg? |
| shRNA | Liposome | 0.05-0.1 mg/kg* | ~0.05-0.1 mg/kg* |
| bi-shRNA | Liposome | 0.05-0.1 mg/kg* | 0.001-0.01 mg/kg* |

MTD = maximum tolerated dose
*predicted based on animal studies

Of a series of bi-shRNA expression vector constructs targeting G12D with a single nucleotide mutation at each position of the guide strand, it was found that the most discriminating knockdown activity for the mutant allele produced by placing a mutant nucleotide at position 2-4. By examining the knockdown effect of additional mismatches at other positions of the guide strand it was determined that the process was sequence-specific.

The systematic analysis of bi-functional shRNA knockdown of the present invention places the most effective discriminating positions at positions 2-4 (the seed region) of the guide strand in contrast to most siRNA based RNAi placing the most effective single nucleotide discriminating position at the central region of the guide strand.

Similar constructs were made for G12V, G12R and G12C mutations and they are effective in the knockdown of their respective target mutant alleles. G12R specific constructs cross-react with G12C mutants and all were found to be functional.

Selected constructs were further compared to control vector on KRAS knockdown using HEK-293 cells wild-type (wt), PANC-1 cells (G12D allele) and MiaPaCa2 cells (G12C allele). G12D and G12C selective bi-shRNA expression vectors did not reduce KRAS expression in HEK-293 in contrast to reduction of KRAS expression in PANC-1 cell and MiaPaCa2 cell, respectively.

Using the teachings herein further test constructs can be made and used with appropriate KRAS mutant expressing cell lines at protein knockdown level and at signal transduction level to further proof specificity of knockdown.

A single expression construct with multimeric bi-shRNA units capable of knocking down G12D, G12V, G12R and G12C is going to be tested for effectiveness and specificity in vitro and in vivo.

Figure 8:
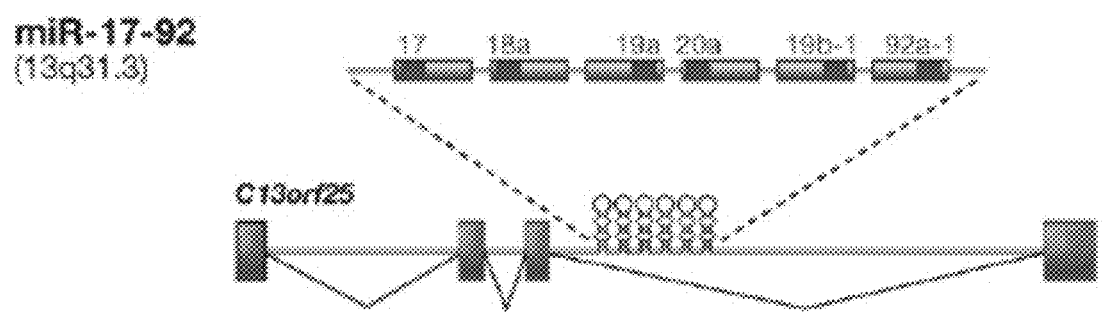
FIG. 8 is a figure that shows an miR-17-92 cluster with 6 miRNAs in tandem.

Construction of multimeric bi-shRNA with triple knockdown capability in one vector using miR-17-92 cluster sequences. FIG. 8 shows the miR-17-92 cluster has 6 miRNAs in tandem.

The sequence in the region is obtained from gi|47076873|dbj|AB176708.1| *Homo sapiens* C13orf25 v_2 mRNA, complete cds, miR-91-precursor-13 micro RNA, microRNA miR-91, microRNA miR-17, miR-18-precursor-13 micro RNA, microRNA miR-18, miR-19a-precursor-13 micro RNA, microRNA miR-19a, microRNA miR-20, miR-19b-precursor-13 micro RNA, microRNA miR-19b, miR-92-precursor-13 micro RNA, microRNA miR-92.

SEQ ID NO.: 57

```
TTTCTTCCCCATTAGGGATTATGCTGAATTTGTATGGTTTATAGTTGTTAGAGTTTGAGGTGTTAATTCT
AATTATCTATTTCAAATTTAGCAGGAAAAAAGAGAACATCACCTTGTAAAACTGAAGATTGTGACCAGTC
AGAATAATGTCAAAGTGCTTACAGTGCAGGTAGTGATATGTGCATCTACTGCAGTGAAGGCACTTGTAGC
ATTATGGTGACAGCTGCCTCGGGAAGCCAAGTTGGGCTTTAAAGTGCAGGGCCTGCTGATGTTGAGTGCT
TTTTGTTCTAAGGTGCATCTAGTGCAGATAGTGAAGTAGATTAGCATCTACTGCCCTAAGTGCTCCTTCT
GGCATAAGAAGTTATGTATTCATCCAATAATTCAAGCCAAGCAAGTATATAGGTGTTTTAATAGTTTTTG
TTTGCAGTCCTCTGTTAGTTTTGCATAGTTGCACTACAAGAAGAATGTAGTTGTGCAAATCTATGCAAAA
CTGATGGTGGCCTGCTATTTCCTTCAAATGAATGATTTTTACTAATTTTGTGTACTTTTATTGTGTCGAT
GTAGAATCTGCCTGGTCTATCTGATGTGACAGCTTCTGTAGCACTAAAGTGCTTATAGTGCAGGTAGTGT
TTAGTTATCTACTGCATTATGAGCACTTAAAGTACTGCTAGCTGTAGAACTCCAGCTTCGGCCTGTCGCC
CAATCAAACTGTCCTGTTACTGAACACTGTTCTATGGTTAGTTTTGCAGGTTTGCATCCAGCTGTGTGAT
ATTCTGCTGTGCAAATCCATGCAAAACTGACTGTGGTAGTGAAAAGTCTGTAGAAAAGTAAGGGAAACTC
AAACCCCTTTCTACACAGGTTGGGATCGGTTGCAATGCTGTGTTTCTGTATGGTATTGCACTTGTCCCGG
CCTGTTGAGTTTGGTGGGATTGTGACCAGAAGATTTTGAAAATTAAATATTACTGAAGATTTCGACTTC
CACTGTTAAATGTACAAGATACATGAAATATTAAAGAAAATGTGTAACTTTTTGTGTAAATACATCTTGT
```

The bold and underlined regions are micro RNA sequences and the italic regions are gap sequences between each micro RNA cistron.

Two sets of triple bi-shRNA multimeric constructs were made to test the knockdown on three different KRAS mutations. The first set maintains miR-30a backbone stem-loop structure and using the miR-17-92 cluster gap sequences. The second set is using miR-17-92 cluster native stem-loop structure backbone and substitute miRNA sequences with bi-shRNA targeting sequences. Two combinations of triple were constructed for each set, pGBI-129 and pGBI-130 are with miR30a backbone in miR-17-92 gap sequences, while pGBI-131 and pGBI-132 are with miR-17-92 backbone and gap sequences. The order of bi-shRNA are G12D-G12V-G12R for pGBI-129 and pGBI-131. The order of bi-shRNA are G12C-G12D-G12R for pGBI-130 and pGBI-132. The sequences are shown below.

Using miR-17-92 Gap sequence with miR-30a backbone, the bold letters are miR30a backbone sequences, the Courier new letters are miR-17-92 gap sequences, the bold italic underlined letters are KRAS targeting sequences, the lower case sequences at each end are insertion restriction site sequences.

pGBI-129 (G12D-G12V-G12R):

(SEQ ID NO.: 53)

```
cgtcgtcgacTTTCTTCCCCATTAGGGATTATGCTGAATTTGTATGGTTTATAGTTGTTAGAGTTTGAGGTGTTA
ATTCTAATTATCTATTTCAAATTTAGCAGGAAAAAAGAGAACATCACCTTGTAAAACTGAAGATTGTGACCATCGAC
TGCTGTTGAAGTGAGCGCCGTGGTAGTTGGAGCTGATGTAGTGAAGCCACAGATGT
ACATCAGCTCCAACTACCACGTTGCCTACTGCCTCGGAAGCAGCTGCCTCGGGAAGCCAAGTTG
```

GGCTTTAAAGTGCAGGGCCTGCTGATGTTGAGTGCTTTTGCTGTTGAAGTGAGCGCC*GTGGTAGTCTT*

*AGCTAATG*TAGTGAAGCCACAGATGTA*C*ATCAGCTCCAACTACCACGTTGCCTACTGC

CTCGGAAGCTTAATAAAGGATCTTTTATTTTCATTGGCTAAGAAGTTATGTATTCATCCAATAA

TTCAAGCCAAGCAAGTATATAGGTGTTTTAATAGTTTTTGTTTTCGACTGCTGTTGAAGTGAGCGC*T*

*GGTAGTTGGAGCTGTTGG*TAGTGAAGCCACAGATGTA*C*CAACAGCTCCAACTACCAGT

TGCCTACTGCCTCGGAAGCTATTTCCTTCAAATGAATGATTTTTACTAATTTTGTGTACTTTTATTGTGTC

GATGTAGAATCTGCCTGGTCTATCTGATGTGACAGCTTCTGCTGTTGAAGTGAGCGCC*TGGTAGTTAC*

*TGCTATTGG*TAGTGAAGCCACAGATGTA*C*CAACAGCTCCAACTACCAGTTGCCTACTG

CCTCGGAAGCTTAATAAAGGATCTTTTATTTTCATTGGCTAGCTGTAGAACTCCAGCTTCGGCC

TGTCGCCCAATCAAACTGTCCTGTTACTGAATCGACTGCTGTTGAAGTGAGCGCC*GTGGTAGTTG*

*GAGCTCGTG*TAGTGAAGCCACAGATGTA*C*ACGAGCTCCAACTACCACGTTGCCTACT

GCCTCGGAAGCAAAAGTCTGTAGAAAAGTAAGGGAAACTCAAACCCGCTGTTGAAGTGAGCGCC*GT*

*GGTAGTACTAGCTAGTG*TAGTGAAGCCACAGATGTA*C*ACGAGCTCCAACTACCACGTT

GCCTACTGCCTCGGAAGCTTAATAAAGGATCTTTTATTTTCATTGGCTGGGGATTGTGAC

CAGAAGATTTTGAAAATTAAATATTACTGAAGATTTCGACTTCCACTGTTAAATGTACAAGATACATGAAATAT

TAAAGAAAATGTGTAACTTTTTGTGTAAATACATCTTGTgcggccgcggat pGBI-130 (G12C-G12D-G12R):

(SEQ ID NO.: 54)

cgtcgtcgacTTTCTTCCCCATTAGGGATTATGCTGAATTTGTATGGTTTATAGTTGTTAGAGTTTGAGGTGTTA

ATTCTAATTATCTATTTCAAATTTAGCAGGAAAAAAGAGAACATCACCTTGTAAAACTGAAGATTGTGACCATCGAC

TGCTGTTGAAGTGAGCGCC*TGTGGTAGTTGGAGCTTGT*TAGTGAAGCCACAGATGT

A*A*CAAGCTCCAACTACCACAGTTGCCTACTGCCTCGGAAGCAGC**TGCCTCGGGAAGCCAAGTTG

GGCTTTAAAGTGCAGGGCCTGCTGATGTTGAGTGCTTTTGCTGTTGAAGTGAGCGCC*TGTGGTAGACT*

*GAGCTAGT*TAGTGAAGCCACAGATGTA*A*CAAGCTCCAACTACCACAGTTGCCTACTG

CCTCGGAAGCTTAATAAAGGATCTTTTATTTTCATTGGCTAAGAAGTTATGTATTCATCCAATA

ATTCAAGCCAAGCAAGTATATAGGTGTTTTAATAGTTTTTGTTTTCGACTGCTGTTGAAGTGAGCGCC*G*

*TGGTAGTTGGAGCTGATG*TAGTGAAGCCACAGATGTA*C*ATCAGCTCCAACTACCACGT

TGCCTACTGCCTCGGAAGCTATTTCCTTCAAATGAATGATTTTTACTAATTTTGTGTACTTTTATTGTGTC

GATGTAGAATCTGCCTGGTCTATCTGATGTGACAGCTTCTGCTGTTGAAGTGAGCGCC*GTGGTAGTCT*

*TAGCTAATG*TAGTGAAGCCACAGATGTA*C*ATCAGCTCCAACTACCACGTTGCCTACTG

CCTCGGAAGCTTAATAAAGGATCTTTTATTTTCATTGGCTAGCTGTAGAACTCCAGCTTCGGCC

TGTCGCCCAATCAAACTGTCCTGTTACTGAATCGACTGCTGTTGAAGTGAGCGCC*TGGTAGTTGG*

*AGCTGTTGG*TAGTGAAGCCACAGATGTA*C*CAACAGCTCCAACTACCAGTTGCCTACT

GCCTCGGAAGCAAAAGTCTGTAGAAAAGTAAGGGAAACTCAAACCCGCTGTTGAAGTGAGCGCC*TG*

*GTAGTTACTGCTATTGG*TAGTGAAGCCACAGATGTA*C*CAACAGCTCCAACTACCAGT

GCCTACTGCCTCGGAAGCTTAATAAAGGATCTTTTATTTTCATTGGCTGGGGATTGTGAC

CAGAAGATTTTGAAAATTAAATATTACTGAAGATTTCGACTTCCACTGTTAAATGTACAAGATACATGAAATATTA

AAGAAAATGTGTAACTTTTTGTGTAAATACATCTTGTgcggccgcggat

Using miR-17-92 backbone, the bold letters are KRAS targeting sequences replacing the miR-17-92 targeting sequences. The lower case letters at each end are the insertion restriction enzyme site sequences.

```
pGBI-131(G12D-G12V-G12R):
                                                    (SEQ ID NO.: 55)
cgtcgtcgacCTTTCTTCCCCATTAGGGATTATGCTGAATTTGTATGGTTTATAGTTGTTAGAGTTTGAGGTGTTA

ATTCTAATTATCTATTTCAAATTTAGCAGGAAAAAAGAGAACATCACCTTGTAAAACTGAAGATTGTGACCAGTCA

GAATAATGTGTGGTAGTTGGAGCTGATGTGATATGTGCATCTCATCAGCTCCAACTACCACCATTATGGTGACAGC

TGCCTCGGGAAGCCAAGTTGGGCTTTAAAGTGCAGGGCCTGCTGATGTTGAGTGCTTTTTGTTCGTGGTAGTCTTA

GCTAATGTGAAGTAGATTAGCATCTCATCAGCTCCAACTACCACCATAAGAAGTTATGTATTCATCCAATAATTCA

AGCCAAGCAAGTATATAGGTGTTTTAATAGTTTTTGTTTGCAGTCCTCTGTTTGGTAGTTGGAGCTGTTGGAGAAG

AATGTAGTCCAACAGCTCCAACTACCATGGTGGCCTGCTATTTCCTTCAAATGAATGATTTTTACTAATTTTGTGT

ACTTTTATTGTGTCGATGTAGAATCTGCCTGGTCTATCTGATGTGACAGCTTCTGTAGCACTTGGTAGTTACTGCT

ATTGGTGTTTAGTTATCTCCAACAGCTCCAACTACCATACTGCTAGCTGTAGAACTCCAGCTTCGGCCTGTCGCCC

AATCAAACTGTCCTGTTACTGAACACTGTTCTATGGTTGTGGTAGTTGGAGCTCGTGTGTGATATTCTGCCACG

AGCTCCAACTACCACCTGTGGTAGTGAAAAGTCTGTAGAAAAGTAAGGGAAACTCAAACCCCTTTCTACACGTGGT

AGTACTAGCTAGTGGTGTTTCTGTATGGCACGAGCTCCAACTACCACTGAGTTTGGTGGGGATTGTGACCAGAAGA

TTTTGAAAATTAAATATTACTGAAGATTTCGACTTCCACTGTTAAATGTACAAGATACATGAAATATTAAAGAAAA

TGTGTAACTTTTTGTGTAAATACATCTTGTgcggccgcggat pGBI-132 (G12C-G12D-G12V):
                                                    (SEQ ID NO.: 56)
cgtcgtcgaCTTTCTTCCCCATTAGGGATTATGCTGAATTTGTATGGTTTATAGTTGTTAGAGTTTGAGGTGTTAA

TTCTAATTATCTATTTCAAATTTAGCAGGAAAAAAGAGAACATCACCTTGTAAAACTGAAGATTGTGACCAGTCAG

AATAATGTTGTGGTAGTTGGAGCTTGTTGATATGTGCATCTACAAGCTCCAACTACCACACATTATGGTGACAGCT

GCCTCGGGAAGCCAAGTTGGGCTTTAAAGTGCAGGGCCTGCTGATGTTGAGTGCTTTTTGTTCTGTGGTAGACTGA

GCTAGTTGAAGTAGATTAGCATCTACAAGCTCCAACTACCACACATAAGAAGTTATGTATTCATCCAATAATTCAA

GCCAAGCAAGTATATAGGTGTTTTAATAGTTTTTGTTTGCAGTCCTCTGTTGTGGTAGTTGGAGCTGATGAGAAGA

ATGTAGTCATCAGCTCCAACTACCACTGGTGGCCTGCTATTTCCTTCAAATGAATGATTTTTACTAATTTTGTGTA

CTTTTATTGTGTCGATGTAGAATCTGCCTGGTCTATCTGATGTGACAGCTTCTGTAGCACTGTGGTAGTCTTAGCT

AATGTGTTTAGTTATCTCATCAGCTCCAACTACCACTACTGCTAGCTGTAGAACTCCAGCTTCGGCCTGTCGCCCA

ATCAAACTGTCCTGTTACTGAACACTGTTCTATGGTTTGGTAGTTGGAGCTGTTGGTGTGTGATATTCTGCCCAAC

AGCTCCAACTACCACTGTGGTAGTGAAAAGTCTGTAGAAAAGTAAGGGAAACTCAAACCCCTTTCTACACTGGTAG

TTACTGCTATTGGGTGTTTCTGTATGGCCAACAGCTCCAACTACCATGAGTTTGGTGGGGATTGTGACCAGAAGAT

TTTGAAAATTAAATATTACTGAAGATTTCGACTTCCACTGTTAAATGTACAAGATACATGAAATATTAAAGAAAAT

GTGTAACTTTTTGTGTAAATACATCTTGTgcggccgcggat
```

Figure 9:
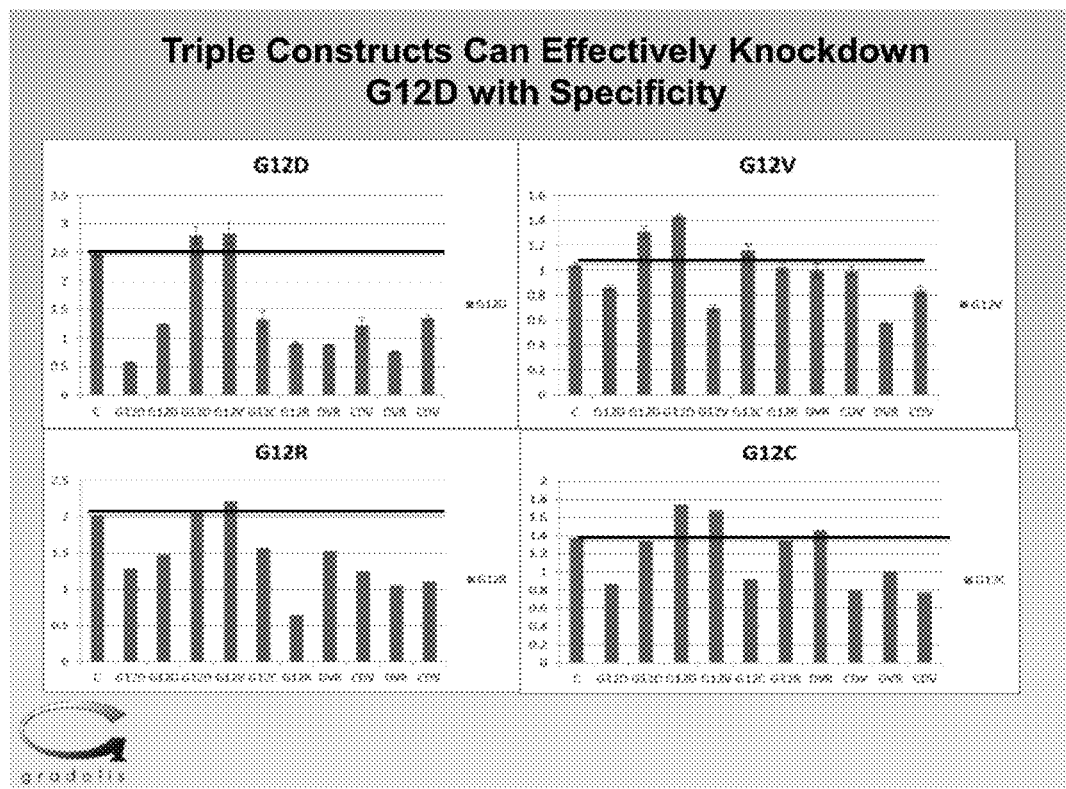
FIG. 9 shows the result of the triple constructs tested with reporter test vectors to compare knockdown efficiency with their singlet counterpart.

Multiple insert constructs. The inserts sequences shown above were synthesized in their entirety by gene synthesis method and cloned into pUMVC3 vector. In one example, triple constructs were first tested with reporter test vectors to compare knockdown efficiency with their singlet counterpart. FIG. 9 shows that the triple constructs can effectively knockdown G12D reporter as well as singlet construct (top left panel, 8-11$^{th}$ bar vs. 2-3$^{rd}$ bar). The pGBI-131 (tip right panel, 10th bar) can knockdown G12V as well as the singlet (5$^{th}$ bar). The triple for G12R did not perform knockdown as well as singlet (lower left panel, 8-11$^{th}$ bar vs. 7$^{th}$ bar). The three of the triple performed better than singlet for G12C (lower right panel, 9-11$^{th}$ bar vs 6$^{th}$ bar). The skilled artisan will recognize that the constructs can include 1, 2, 3, 4, 5, 6, 7, 8, 9, 10, 12, 13, 14, 15, 16, 17, 18, 20, 21, 25, 50, 75, or 100 inserts. The inserts can be included in 1, 2, 3, 5, 6, 7, 8, 9 or 10 different vectors having different types (or overlapping) of promoters, origins of replication, antibiotic or other resistance genes, selectivity domains or genes, variable expression domains, recombination domains, and other domains necessary for expression of the construct and propagation of the vectors. In general, the triple constructs shown here can perform knockdown as well as the singlet. The knockdown efficiency varies between the four triplet constructs tested.

Figures 10, 11:
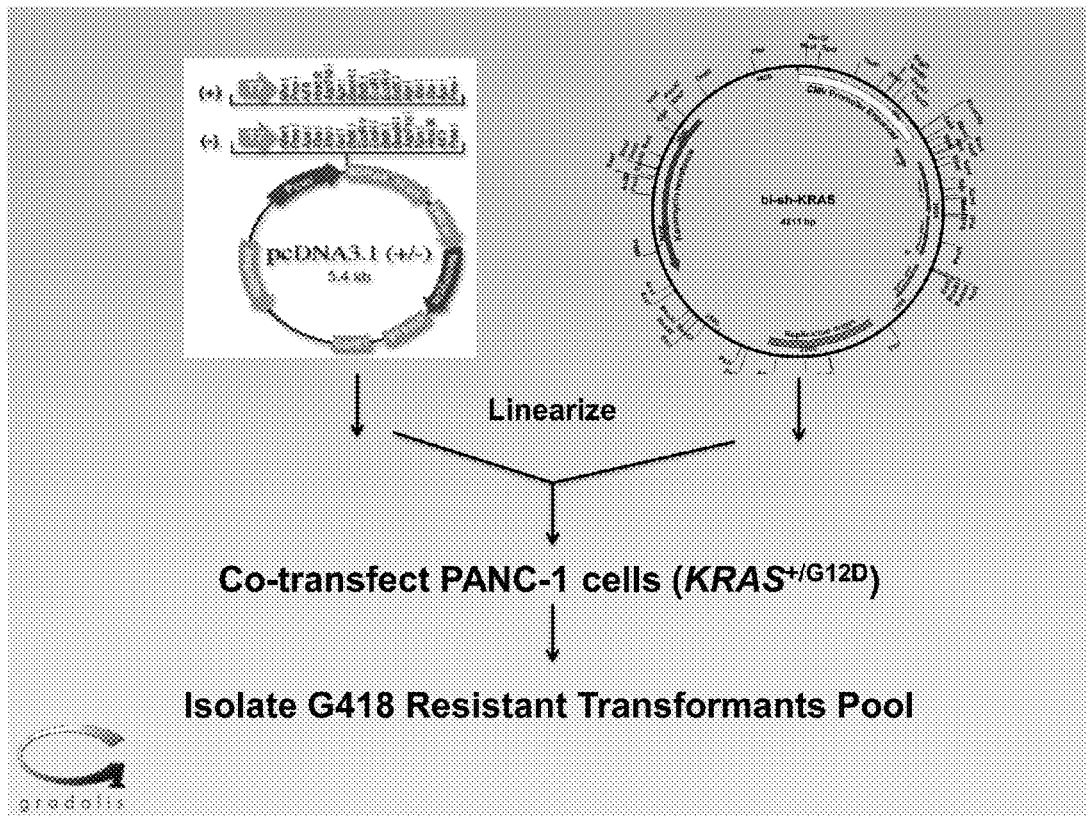
FIG. 10 shows a scheme for making cells that comprise the one or more bifunctional shRNAs of the present invention.
FIG. 11 shows the results from using triple constructs with miR-17-92 gap sequences (pGBI-129 and pGBI-130) can knockdown mutant (Lanes 4 and 5) while triple constructs with miR-17-92 backbone sequences (pGBI-131 and pGBI-132) can very efficiently knockdown mutant (Lanes 6 and 7).

We next test the knockdown efficiency of the triplet with PANC-1 cells. PANC-1 cells has KRAS$^{wt/G12D}$ genotype with one wild type allele and one G12D mutant allele. We tested whether the triples are effective in knocking down the G12D expression while not affecting the wild type expression. In order to test all cell population, we established transformants with G418 resistant vector. The majority of G418 resistant transformants in the pool should constitutively express the bi-sh-KRAS. FIG. 10 shows the scheme for establishing transformants.

Established pools of transformants were tested for KRAS mRNA population. We used the restriction fragment length polymorphism (RFLP) to discriminate the wild type transcripts vs. the mutant transcripts. BstXI restriction site were introduced during PCR amplification, as the result BstXI will cut the wild type fragments while leaving mutation containing fragments intact. BstXI digested PCR products was separated on a 4% agarose gel, the upper band represent mutant population and the lower band represent the wild type population. FIG. 11 shows that the triple constructs with miR-17-92 gap sequences (pGBI-129 and pGBI-130) can only mildly knockdown mutant (Lanes 4 and 5) while triple constructs with miR-17-92 backbone sequences (pGBI-131 and pGBI-132) can very efficiently knockdown mutant (Lanes 6 and 7). Interestingly and unexpectedly, pGBI-131 and pGBI-132 not only greatly reduced the mutant mRNA population but also enhanced the wild type mRNA expression. The triple constructs pGBI-131 and pGBI-132 can effectively and selectively reduced the G12D mutant mRNA and return the wild type expression to normal level.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 11, 12, 13, 14 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Ohnishi Y, Tokunaga K, Kaneko K, Hohjoh H. Assessment of allele-specific gene silencing by RNA interference with mutant and wild-type reporter alleles. J RNAi Gene Silencing. 2006 Feb. 28; 2(1):154-60.
2. Huang H, Qiao R, Zhao D, Zhang T, Li Y, Yi F, Lai F, Hong J, Ding X, Yang Z, Zhang L, Du Q, Liang Z. Profiling of mismatch discrimination in RNAi enabled rational design of allele-specific siRNAs. Nucleic Acids Res. 2009 December; 37(22):7560-9.
3. Schwarz D S, Ding H, Kennington L, Moore J T, Schelter J, Burchard J, Linsley P S, Aronin N, Xu Z, Zamore P D. Designing siRNA that distinguish between genes that differ by a single nucleotide. PLoS Genet. 2006 Sep. 8; 2(9): e140.
4. Geng C M, Ding H L. Design of functional small interfering RNAs targeting amyotrophic lateral sclerosis-associated mutant alleles. Chin Med J (Engl). 2011 January; 124(1):106-10.
5. Brummelkamp T R, Bernards R, Agami R. Stable suppression of tumorigenicity by virus-mediated RNA interference. Cancer Cell. 2002 September; 2(3):243-7.
6. Fleming J B, Shen G L, Holloway S E, Davis M, Brekken R A. Molecular consequences of silencing mutant K-ras in pancreatic cancer cells: justification for K-ras-directed therapy. Mol Cancer Res. 2005 July; 3(7):413-23.

7. Zhang Z, Jiang G, Yang F, Wang J. Knockdown of mutant K-ras expression by adenovirus-mediated siRNA inhibits the in vitro and in vivo growth of lung cancer cells. Cancer Biol Ther. 2006 November; 5(11):1481-6.
8. Smakman N, Veenendaal L M, van Diest P, Bos R, Offringa R, Borel Rinkes I H, Kranenburg O. Dual effect of Kras (D12) knockdown on tumorigenesis: increased immune-mediated tumor clearance and abrogation of tumor malignancy. Oncogene. 2005 Dec. 15; 24(56):8338-42.
9. Zhang Y A, Nemunaitis J, Samuel S K, Chen P, Shen Y, Tong A W. Antitumor activity of an oncolytic adenovirus-delivered oncogene small interfering RNA. Cancer Res. 2006 Oct. 1; 66(19):9736-43.
10. Sierant M, Paduszynska A, Kazmierczak-Baranska J, Nacmias B, Sorbi S, Bagnoli S, Sochacka E, Nawrot B. Specific Silencing of L392V PSEN1 Mutant Allele by RNA Interference. Int J Alzheimers Dis. 2011 Apr. 7; 2011: 809218.
11. de Yñnigo-Mojado L, Martin-Ruiz I, Sutherland J D. Efficient allele-specific targeting of LRRK2 R1441 mutations mediated by RNAi. PLoS One. 2011; 6(6):e21352.
12. Takahashi M, Watanabe S, Murata M, Furuya H, Kanazawa I, Wada K, Hohjoh H. Tailor-made RNAi knockdown against triplet repeat disease-causing alleles. Proc Natl Acad Sci USA. 2010 Dec. 14; 107(50):21731-6.
13. Pfister E L, Kennington L, Straubhaar J, Wagh S, Liu W, DiFiglia M, Landwehrmeyer B, Vonsattel J P, Zamore P D, Aronin N. Five siRNAs targeting three SNPs may provide therapy for three-quarters of Huntington's disease patients. Curr Biol. 2009 May 12; 19(9):774-8.
14. Rao D D, Maples P B, Senzer N, Kumar P, Wang Z, Pappen B O, Yu Y, Haddock C, Jay C, Phadke A P, Chen S, Kuhn J, Dylewski D, Scott S, Monsma D, Webb C, Tong A, Shanahan D, Nemunaitis J. Enhanced target gene knockdown by a bifunctional shRNA: a novel approach of RNA interference. Cancer Gene Ther. 2010 November; 17(11): 780-91.
15. Rao D D, Senzer N, Wang Z, Kumar P, Jay C M, Nemunaitis J. Bi-functional Short Hairpin RNA (bi-shRNA): Design and Pathway to Clinical Application. Methods Mol. Biol. 2012.

What is claimed is:

1. A bifunctional shRNAs capable of reducing an expression of a mutated K-ras gene, wherein at least one target site sequence of the bifunctional RNA molecule is located within the K-ras gene and wherein the bifunctional RNA molecule is capable of activating a cleavage-dependent and a cleavage-independent RNA-induced silencing complex for reducing the expression level of mutated K-ras, without reducing normal K-ras expression, wherein the bifunctional shRNA comprises the sequence of SEQ ID NO: 56.

2. The bifunctional shRNAs of claim 1, wherein at least one target site sequence is within a human K-ras gene cDNA sequence (SEQ ID NOS: 27, 28 and 30).

3. An expression vector comprising:
a promoter; and
a nucleic acid insert operably linked to the promoter, wherein the insert encodes one or more shRNA capable of inhibiting an expression of at least one target gene that is a mutated K-ras gene via RNA interference;
wherein the one or more shRNA comprise a bifunctional RNA molecule that activates a cleavage-dependent and a cleavage-independent RNA-induced silencing complex for reducing the expression level of the mutated K-ras, without reducing normal K-ras expression, wherein the bifunctional shRNA comprises the sequence of SEQ ID NO: 56.

4. The expression vector of claim 3, wherein the target gene sequence comprises SEQ ID NOS: 27, 28 and 30.

5. The expression vector of claim 3, wherein a sequence arrangement for the shRNA comprises a 5' stem arm-19 nucleotide target, which is K-ras-TA-15 nucleotide loop-19 nucleotide target complementary sequence-3' stem arm-Spacer-5' stem arm-19 nucleotide target variant-TA-15 nucleotide loop-19 nucleotide target complementary sequence-3' stem arm.

6. The expression vector of claim 3, wherein the vector comprises 1, 2, 3, 4, 5, 6, 7, 8, 9, 10, 12, 13, 14, 15, 16, 17, 18, 20, 21, 25, 50, 75, or 100 copies of bifunctional shRNAs inserts capable of reducing an expression of one or more mutated K-ras genes.

7. The expression vector of claim 3, wherein at least one shRNA has a target site sequence that is within a mutated K-ras gene cDNA sequence.

8. A therapeutic delivery system comprising:
a therapeutic agent carrier; and
an expression vector comprising a promoter and a nucleic acid insert operably linked to the promoter, the nucleic acid insert encoding one or more short hairpin RNA (shRNA) capable inhibiting an expression of a target gene sequence that is mutated K-ras gene via RNA interference;
wherein the one or more shRNA comprise a bifunctional RNA molecule that activates a cleavage-dependent and a cleavage-independent RNA-induced silencing complex for reducing the expression level of the mutated K-ras, without reducing normal K-ras expression, wherein the bifunctional shRNA comprises the sequence of SEQ ID NO: 56.

9. The delivery system of claim 8, wherein the therapeutic agent carrier is a compacted DNA nanoparticle, or a compacted DNA nanoparticle with one or more polycations.

10. The delivery system of claim 9, wherein the one or more polycations is a 10 kDA polyethylene glycol (PEG)-substituted cysteine-lysine 3-mer peptide (CK30PEG10k).

11. The delivery system of claim 9, wherein the compacted DNA nanoparticles are further encapsulated in at least one of a liposome, a reversibly masked liposome, or a bilamellar invaginated vesicle (BIV).

12. The delivery system of claim 8, wherein the target gene sequence comprises SEQ ID NOS: 27, 28 and 30.

13. An expression vector comprising 1, 2, 3, 4, 5, 6, 7, 8, 9, 10, 12, 13, 14, 15, 16, 17, 18, 20, 21, 25, 50, 75, or 100 bifunctional shRNAs inserts capable of reducing an expression of a mutant K-ras gene; wherein at least one target site sequence of the bifunctional RNA molecule is located within the mutant K-ras gene, wherein the bifunctional RNA molecule is capable of activating a cleavage-dependent and a cleavage-independent RNA-induced silencing complex for reducing the expression level of the mutant K-ras, without reducing normal K-ras expression, wherein the bifunctional shRNA comprises the sequence of SEQ ID NO: 56.

14. The expression vector of claim 13, wherein the bifunctional shRNA comprise triplet inserts that target specific K-ras mutations selected from G12C-G12D-G12V.

15. The expression vector of claim 13, wherein the bifunctional shRNA comprise triplet inserts that target specific K-ras mutations selected from SEQ ID NOS: 27, 28 and 30.

16. A cell comprising an expression unit that includes 1, 2, 3, 4, 5, 6, 7, 8, 9, 10, 12, 13, 14, 15, 16, 17, 18, 20, 21, 25, 50, 75, or 100 bifunctional shRNAs inserts capable of reducing an expression of a mutant K-ras gene; wherein at least one target site sequence of the bifunctional RNA molecule is located within the K-ras gene, wherein the bifunctional RNA molecule is capable of activating a cleavage-dependent and a cleavage-independent RNA-induced silencing complex for reducing the expression level of K-ras, without reducing normal K-ras expression, wherein the bifunctional shRNA comprises the sequence of SEQ ID NO: 56.

17. The cell of claim 16, wherein the bifunctional shRNA increases the relative expression of wild-type K-ras versus mutant K-ras.

\* \* \* \* \*

SEQUENCE LISTING

```
<160> NUMBER OF SEQ ID NOS: 58

<210> SEQ ID NO 1
<211> LENGTH: 245
<212> TYPE: DNA
<213> ORGANISM: Homo sapiens

<400> SEQUENCE: 1
tcgactgctg ttgaagtgag cgcctgtggt agttggagct gattagtgaa gccacagatg    60
taatcagctc caactaccac agttgcctac tgcctcggaa gcagctcact acattactca   120
gctgttgaag tgagcgcctg tggtaggaag agatgattag tgaagccaca gatgtaatca   180
gctccaacta ccacagttgc ctactgcctc ggaagcttaa taaggatct tttattttca    240 ttggc                                                               245

<210> SEQ ID NO 2
<211> LENGTH: 245
<212> TYPE: DNA
<213> ORGANISM: Homo sapiens

<400> SEQUENCE: 2
tcgactgctg ttgaagtgag cgccgtggta gttggagctg atgtagtgaa gccacagatg    60
tacatcagct ccaactacca cgttgcctac tgcctcggaa gcagctcact acattactca   120
gctgttgaag tgagcgccgt ggtagtctta gctaatgtag tgaagccaca gatgtacatc   180
agctccaact accacgttgc ctactgcctc ggaagcttaa taaggatct tttattttca    240 ttggc                                                               245

<210> SEQ ID NO 3
<211> LENGTH: 245
<212> TYPE: DNA
<213> ORGANISM: Homo sapiens

<400> SEQUENCE: 3
tcgactgctg ttgaagtgag cgcctggtag ttggagctga tggtagtgaa gccacagatg    60
taccatcagc tccaactacc agttgcctac tgcctcggaa gcagctcact acattactca   120
gctgttgaag tgagcgcctg gtagttactg ctaatggtag tgaagccaca gatgtaccat   180
```

| cagctccaac taccagttgc ctactgcctc ggaagcttaa taaaggatct tttattttca | 240 |
| ttggc | 245 |

<210> SEQ ID NO 4
<211> LENGTH: 245
<212> TYPE: DNA
<213> ORGANISM: Homo sapiens

<400> SEQUENCE: 4

| tcgactgctg ttgaagtgag cgccggtagt tggagctgat ggctagtgaa gccacagatg | 60 |
| tagccatcag ctccaactac cgttgcctac tgcctcggaa gcagctcact acattactca | 120 |
| gctgttgaag tgagcgccgg tagttgtctc tgatagctag tgaagccaca gatgtagcca | 180 |
| tcagctccaa ctaccgttgc ctactgcctc ggaagcttaa taaaggatct tttattttca | 240 |
| ttggc | 245 |

<210> SEQ ID NO 5
<211> LENGTH: 245
<212> TYPE: DNA
<213> ORGANISM: Homo sapiens

<400> SEQUENCE: 5

| tcgactgctg ttgaagtgag cgccgtagtt ggagctgatg gcgtagtgaa gccacagatg | 60 |
| tacgccatca gctccaacta cgttgcctac tgcctcggaa gcagctcact acattactca | 120 |
| gctgttgaag tgagcgccgt agttggagct gatggcgtag tgaagccaca gatgtacgcc | 180 |
| atcagctcca actacgttgc ctactgcctc ggaagcttaa taaaggatct tttattttca | 240 |
| ttggc | 245 |

<210> SEQ ID NO 6
<211> LENGTH: 245
<212> TYPE: DNA
<213> ORGANISM: Homo sapiens

<400> SEQUENCE: 6

| tcgactgctg ttgaagtgag cgcctagttg gagctgatgg cgttagtgaa gccacagatg | 60 |
| taacgccatc agctccaact agttgcctac tgcctcggaa gcagctcact acattactca | 120 |
| gctgttgaag tgagcgccta gttggatgag atgacgttag tgaagccaca gatgtaacgc | 180 |
| catcagctcc aactagttgc ctactgcctc ggaagcttaa taaaggatct tttattttca | 240 |
| ttggc | 245 |

<210> SEQ ID NO 7
<211> LENGTH: 245
<212> TYPE: DNA
<213> ORGANISM: Homo sapiens

<400> SEQUENCE: 7

| tcgactgctg ttgaagtgag cgccagttgg agctgatggc gtatagtgaa gccacagatg | 60 |
| tatacgccat cagctccaac tgttgcctac tgcctcggaa gcagctcact acattactca | 120 |
| gctgttgaag tgagcgccag ttggagacta tggagtatag tgaagccaca gatgtatacg | 180 |
| ccatcagctc caactgttgc ctactgcctc ggaagcttaa taaaggatct tttattttca | 240 |
| ttggc | 245 |

<210> SEQ ID NO 8
<211> LENGTH: 245

```
<212> TYPE: DNA
<213> ORGANISM: Homo sapiens

<400> SEQUENCE: 8
tcgactgctg ttgaagtgag cgccgttgga gctgatggcg tagtagtgaa gccacagatg    60
tactacgcca tcagctccaa cgttgcctac tgcctcggaa gcagctcact acattactca   120
gctgttgaag tgagcgccgt tgaagcacgt ggtgtagtag tgaagccaca gatgtactac   180
gccatcagct ccaacgttgc ctactgcctc ggaagcttaa taaggatctt ttatttttca   240
ttggc                                                              245

<210> SEQ ID NO 9
<211> LENGTH: 245
<212> TYPE: DNA
<213> ORGANISM: Homo sapiens

<400> SEQUENCE: 9
tcgactgctg ttgaagtgag cgccttggag ctgatggcgt aggtagtgaa gccacagatg    60
tacctacgcc atcagctcca agttgcctac tgcctcggaa gcagctcact acattactca   120
gctgttgaag tgagcgcctt ggagctatag gtctaggtag tgaagccaca gatgtaccta   180
cgccatcagc tccaagttgc ctactgcctc ggaagcttaa taaggatctt ttatttttca   240
ttggc                                                              245

<210> SEQ ID NO 10
<211> LENGTH: 245
<212> TYPE: DNA
<213> ORGANISM: Homo sapiens

<400> SEQUENCE: 10
tcgactgctg ttgaagtgag cgcctggagc tgatggcgta ggctagtgaa gccacagatg    60
tagcctacgc catcagctcc agttgcctac tgcctcggaa gcagctcact acattactca   120
gctgttgaag tgagcgcctg gagctgtatg cgttcgctag tgaagccaca gatgtagcct   180
acgccatcag ctccagttgc ctactgcctc ggaagcttaa taaggatctt ttatttttca   240
ttggc                                                              245

<210> SEQ ID NO 11
<211> LENGTH: 245
<212> TYPE: DNA
<213> ORGANISM: Homo sapiens

<400> SEQUENCE: 11
tcgactgctg ttgaagtgag cgccgttgga gctgatggcg tagtagtgaa gccacagatg    60
tactatgcca tcagctccaa cgttgcctac tgcctcggaa gcagctcact acattactca   120
gctgttgaag tgagcgccgt tgaagcacgt ggtgtagtag tgaagccaca gatgtactat   180
gccatcagct ccaacgttgc ctactgcctc ggaagcttaa taaggatctt ttatttttca   240
ttggc                                                              245

<210> SEQ ID NO 12
<211> LENGTH: 245
<212> TYPE: DNA
<213> ORGANISM: Homo sapiens

<400> SEQUENCE: 12
tcgactgctg ttgaagtgag cgccttggag ctgatggcgt aggtagtgaa gccacagatg    60
```

```
tacctatgcc atcagctcca agttgcctac tgcctcggaa gcagctcact acattactca      120
gctgttgaag tgagcgcctt ggagctatag gtctaggtag tgaagccaca gatgtaccta      180
tgccatcagc tccaagttgc ctactgcctc ggaagcttaa taaaggatct tttatttca       240 ttggc                                                                  245

<210> SEQ ID NO 13
<211> LENGTH: 245
<212> TYPE: DNA
<213> ORGANISM: Homo sapiens

<400> SEQUENCE: 13
tcgactgctg ttgaagtgag cgcctggagc tgatggcgta ggctagtgaa gccacagatg       60
tagcctatgc catcagctcc agttgcctac tgcctcggaa gcagctcact acattactca      120
gctgttgaag tgagcgcctg gagctgtatg cgttcgctag tgaagccaca gatgtagcct      180
atgccatcag ctccagttgc ctactgcctc ggaagcttaa taaaggatct tttatttca       240 ttggc                                                                  245

<210> SEQ ID NO 14
<211> LENGTH: 245
<212> TYPE: DNA
<213> ORGANISM: Homo sapiens

<400> SEQUENCE: 14
tcgactgctg ttgaagtgag cgccgttgga gctcatggcg tagtagtgaa gccacagatg       60
tactacgcca tgagctccaa cgttgcctac tgcctcggaa gcagctcact acattactca      120
gctgttgaag tgagcgccgt tgaagcacgt ggtgtagtag tgaagccaca gatgtactac      180
gccatgagct ccaacgttgc ctactgcctc ggaagcttaa taaaggatct tttatttca       240 ttggc                                                                  245

<210> SEQ ID NO 15
<211> LENGTH: 245
<212> TYPE: DNA
<213> ORGANISM: Homo sapiens

<400> SEQUENCE: 15
tcgactgctg ttgaagtgag cgccttggag ctcatggcgt aggtagtgaa gccacagatg       60
tacctacgcc atgagctcca agttgcctac tgcctcggaa gcagctcact acattactca      120
gctgttgaag tgagcgcctt ggagctatag gtctaggtag tgaagccaca gatgtaccta      180
cgccatgagc tccaagttgc ctactgcctc ggaagcttaa taaaggatct tttatttca       240 ttggc                                                                  245

<210> SEQ ID NO 16
<211> LENGTH: 245
<212> TYPE: DNA
<213> ORGANISM: Homo sapiens

<400> SEQUENCE: 16
tcgactgctg ttgaagtgag cgcctggagc tcatggcgta ggctagtgaa gccacagatg       60
tagcctacgc catgagctcc agttgcctac tgcctcggaa gcagctcact acattactca      120
gctgttgaag tgagcgcctg gagctgtatg cgttcgctag tgaagccaca gatgtagcct      180
acgccatgag ctccagttgc ctactgcctc ggaagcttaa taaaggatct tttatttca       240 ttggc                                                                  245
```

<210> SEQ ID NO 17
<211> LENGTH: 245
<212> TYPE: DNA
<213> ORGANISM: Homo sapiens

<400> SEQUENCE: 17

```
tcgactgctg ttgaagtgag cgccgtggta gttggagctg ttgtagtgaa gccacagatg      60
tacaacagct ccaactacca cgttgcctac tgcctcggaa gcagctcact acattactca     120
gctgttgaag tgagcgccgt ggtagtctta gctattgtag tgaagccaca gatgtacaac     180
agctccaact accacgttgc ctactgcctc ggaagcttaa taaggatct tttattttca      240
ttggc                                                                 245
```

<210> SEQ ID NO 18
<211> LENGTH: 245
<212> TYPE: DNA
<213> ORGANISM: Homo sapiens

<400> SEQUENCE: 18

```
tcgactgctg ttgaagtgag cgcctggtag ttggagctgt tggtagtgaa gccacagatg      60
taccaacagc tccaactacc agttgcctac tgcctcggaa gcagctcact acattactca     120
gctgttgaag tgagcgcctg gtagttactg ctattggtag tgaagccaca gatgtaccaa     180
cagctccaac taccagttgc ctactgcctc ggaagcttaa taaggatct tttattttca      240
ttggc                                                                 245
```

<210> SEQ ID NO 19
<211> LENGTH: 245
<212> TYPE: DNA
<213> ORGANISM: Homo sapiens

<400> SEQUENCE: 19

```
tcgactgctg ttgaagtgag cgcctgtggt agttggagct cgttagtgaa gccacagatg      60
taacgagctc caactaccac agttgcctac tgcctcggaa gcagctcact acattactca     120
gctgttgaag tgagcgcctg tggtagactg agctagttag tgaagccaca gatgtaacga     180
gctccaacta ccacagttgc ctactgcctc ggaagcttaa taaggatct tttattttca      240
ttggc                                                                 245
```

<210> SEQ ID NO 20
<211> LENGTH: 245
<212> TYPE: DNA
<213> ORGANISM: Homo sapiens

<400> SEQUENCE: 20

```
tcgactgctg ttgaagtgag cgccgtggta gttggagctc gtgtagtgaa gccacagatg      60
tacacgagct ccaactacca cgttgcctac tgcctcggaa gcagctcact acattactca     120
gctgttgaag tgagcgccgt ggtagtacta gctagtgtag tgaagccaca gatgtacacg     180
agctccaact accacgttgc ctactgcctc ggaagcttaa taaggatct tttattttca      240
ttggc                                                                 245
```

<210> SEQ ID NO 21
<211> LENGTH: 245
<212> TYPE: DNA
<213> ORGANISM: Homo sapiens

<400> SEQUENCE: 21
tcgactgctg ttgaagtgag cgcctgtggt agttggagct tgttagtgaa gccacagatg    60
taacaagctc caactaccac agttgcctac tgcctcggaa gcagctcact acattactca   120
gctgttgaag tgagcgcctg tggtagactg agctagttag tgaagccaca gatgtaacaa   180
gctccaacta ccacagttgc ctactgcctc ggaagcttaa taaggatct tttattttca   240 ttggc                                                              245

<210> SEQ ID NO 22
<211> LENGTH: 245
<212> TYPE: DNA
<213> ORGANISM: Homo sapiens

<400> SEQUENCE: 22
tcgactgctg ttgaagtgag cgccgtggta gttggagctt gtgtagtgaa gccacagatg    60
tacacaagct ccaactacca cgttgcctac tgcctcggaa gcagctcact acattactca   120
gctgttgaag tgagcgccgt ggtagtctta gcttatgtag tgaagccaca gatgtacaca   180
agctccaact accacgttgc ctactgcctc ggaagcttaa taaggatctt ttattttca    240 ttggc                                                              245

<210> SEQ ID NO 23
<211> LENGTH: 208
<212> TYPE: DNA
<213> ORGANISM: Homo sapiens

<400> SEQUENCE: 23
gctagccacc atgactgaat ataaacttgt ggtagttgga gctggtggcg taggcaagag    60
tgcttccaag gtgtacgacc ccgagcaacg caaacgcatg atcactgggc ctcagtggtg   120
ggctcgctgc aagcaaatga acgtgctgga ctccttcatc aactactatg attccgagaa   180
gcacgccgag gaggcacgtc gtgcctca                                     208

<210> SEQ ID NO 24
<211> LENGTH: 51
<212> TYPE: DNA
<213> ORGANISM: Homo sapiens

<400> SEQUENCE: 24
atgactgaat ataaacttgt ggtagttgga gctgatggcg taggcaagag t            51

<210> SEQ ID NO 25
<211> LENGTH: 208
<212> TYPE: DNA
<213> ORGANISM: Homo sapiens

<400> SEQUENCE: 25
cacttcgcat attaaggtga cgcgtgtggc ctcgaacacc gagcgaccct gcagcgaccc    60
gcttaaaagc ttggcattcc ggtactgttg gtaaagccac catgactgaa tataaacttg   120
tggtagttgg agctgatggc gtaggcaaga gtgccgatgc taagaacatt aagaagggcc   180 ctgctcccctt ctaccctctg gaggatgg                                    208

<210> SEQ ID NO 26
<211> LENGTH: 36
<212> TYPE: DNA
<213> ORGANISM: Homo sapiens

<400> SEQUENCE: 26
cttgtggtag ttggagctgg tggcgtaggc aagagt          36

<210> SEQ ID NO 27
<211> LENGTH: 30
<212> TYPE: DNA
<213> ORGANISM: Homo sapiens

<400> SEQUENCE: 27
cttgtggtag ttggagctga tggcgtaggc          30

<210> SEQ ID NO 28
<211> LENGTH: 30
<212> TYPE: DNA
<213> ORGANISM: Homo sapiens

<400> SEQUENCE: 28
cttgtggtag ttggagctgt tggcgtaggc          30

<210> SEQ ID NO 29
<211> LENGTH: 30
<212> TYPE: DNA
<213> ORGANISM: Homo sapiens

<400> SEQUENCE: 29
cttgtggtag ttggagctcg tggcgtaggc          30

<210> SEQ ID NO 30
<211> LENGTH: 30
<212> TYPE: DNA
<213> ORGANISM: Homo sapiens

<400> SEQUENCE: 30
cttgtggtag ttggagcttg tggcgtaggc          30

<210> SEQ ID NO 31
<211> LENGTH: 19
<212> TYPE: DNA
<213> ORGANISM: Homo sapiens

<400> SEQUENCE: 31
acaccatcaa cctcgacta          19

<210> SEQ ID NO 32
<211> LENGTH: 19
<212> TYPE: DNA
<213> ORGANISM: Homo sapiens

<400> SEQUENCE: 32
caccatcaac ctcgactac          19

<210> SEQ ID NO 33
<211> LENGTH: 19
<212> TYPE: DNA
<213> ORGANISM: Homo sapiens

<400> SEQUENCE: 33
accatcaacc tcgactacc          19

<210> SEQ ID NO 34
<211> LENGTH: 19
<212> TYPE: DNA
<213> ORGANISM: Homo sapiens

<400> SEQUENCE: 34
ccatcaacct cgactaccg                                                        19

<210> SEQ ID NO 35
<211> LENGTH: 19
<212> TYPE: DNA
<213> ORGANISM: Homo sapiens

<400> SEQUENCE: 35
catcaacctc gactaccgc                                                        19

<210> SEQ ID NO 36
<211> LENGTH: 19
<212> TYPE: DNA
<213> ORGANISM: Homo sapiens

<400> SEQUENCE: 36
atcaacctcg actaccgca                                                        19

<210> SEQ ID NO 37
<211> LENGTH: 19
<212> TYPE: DNA
<213> ORGANISM: Homo sapiens

<400> SEQUENCE: 37
tcaacctcga ctaccgcat                                                        19

<210> SEQ ID NO 38
<211> LENGTH: 19
<212> TYPE: DNA
<213> ORGANISM: Homo sapiens

<400> SEQUENCE: 38
caacctcgac taccgcatc                                                        19

<210> SEQ ID NO 39
<211> LENGTH: 19
<212> TYPE: DNA
<213> ORGANISM: Homo sapiens

<400> SEQUENCE: 39
aacctcgact accgcatcc                                                        19

<210> SEQ ID NO 40
<211> LENGTH: 19
<212> TYPE: DNA
<213> ORGANISM: Homo sapiens

<400> SEQUENCE: 40
acctcgacta ccgcatccg                                                        19

<210> SEQ ID NO 41
<211> LENGTH: 19
<212> TYPE: DNA
<213> ORGANISM: Homo sapiens

<400> SEQUENCE: 41
caacctcgac taccgtatc                                                        19

<210> SEQ ID NO 42
<211> LENGTH: 19
<212> TYPE: DNA
<213> ORGANISM: Homo sapiens

```
<400> SEQUENCE: 42
aacctcgact accgtatcc                                                19

<210> SEQ ID NO 43
<211> LENGTH: 19
<212> TYPE: DNA
<213> ORGANISM: Homo sapiens

<400> SEQUENCE: 43
acctcgacta ccgtatccg                                                19

<210> SEQ ID NO 44
<211> LENGTH: 19
<212> TYPE: DNA
<213> ORGANISM: Homo sapiens

<400> SEQUENCE: 44
caacctcgag taccgcatc                                                19

<210> SEQ ID NO 45
<211> LENGTH: 19
<212> TYPE: DNA
<213> ORGANISM: Homo sapiens

<400> SEQUENCE: 45
aacctcgagt accgcatcc                                                19

<210> SEQ ID NO 46
<211> LENGTH: 19
<212> TYPE: DNA
<213> ORGANISM: Homo sapiens

<400> SEQUENCE: 46
acctcgagta ccgcatccg                                                19

<210> SEQ ID NO 47
<211> LENGTH: 19
<212> TYPE: DNA
<213> ORGANISM: Homo sapiens

<400> SEQUENCE: 47
caccatcaac ctcgacaac                                                19

<210> SEQ ID NO 48
<211> LENGTH: 19
<212> TYPE: DNA
<213> ORGANISM: Homo sapiens

<400> SEQUENCE: 48
accatcaacc tcgacaacc                                                19

<210> SEQ ID NO 49
<211> LENGTH: 19
<212> TYPE: DNA
<213> ORGANISM: Homo sapiens

<400> SEQUENCE: 49
acaccatcaa cctcgagca                                                19

<210> SEQ ID NO 50
<211> LENGTH: 19
<212> TYPE: DNA
```

<213> ORGANISM: Homo sapiens

<400> SEQUENCE: 50
caccatcaac ctcgagcac                                                    19

<210> SEQ ID NO 51
<211> LENGTH: 19
<212> TYPE: DNA
<213> ORGANISM: Homo sapiens

<400> SEQUENCE: 51
acaccatcaa cctcgaaca                                                    19

<210> SEQ ID NO 52
<211> LENGTH: 19
<212> TYPE: DNA
<213> ORGANISM: Homo sapiens

<400> SEQUENCE: 52
caccatcaac ctcgaacac                                                    19

<210> SEQ ID NO 53
<211> LENGTH: 1280
<212> TYPE: DNA
<213> ORGANISM: Homo sapiens

<400> SEQUENCE: 53
cgtcgtcgac tttcttcccc attagggatt atgctgaatt tgtatggttt atagttgtta      60
gagtttgagg tgttaattct aattatctat ttcaaattta gcaggaaaaa agagaacatc     120
accttgtaaa actgaagatt gtgaccatcg actgctgttg aagtgagcgc cgtggtagtt     180
ggagctgatg tagtgaagcc acagatgtac atcagctcca actaccacgt tgcctactgc     240
ctcggaagca gctgcctcgg aagccaagt tgggctttaa agtgcagggc ctgctgatgt      300
tgagtgcttt tgctgttgaa gtgagcgccg tggtagtctt agctaatgta gtgaagccac     360
agatgtacat cagctccaac taccacgttg cctactgcct cggaagctta ataaaggatc     420
ttttattttc attggctaag aagttatgta ttcatccaat aattcaagcc aagcaagtat     480
ataggtgttt taatagtttt tgttttcgac tgctgttgaa gtgagcgcct ggtagttgga     540
gctgttggta gtgaagccac agatgtacca acagctccaa ctaccagttg cctactgcct     600
cggaagctat ttccttcaaa tgaatgattt ttactaattt tgtgtacttt tattgtgtcg     660
atgtagaatc tgcctggtct atctgatgtg acagcttctg ctgttgaagt gagcgcctgg     720
tagttactgc tattggtagt gaagccacag atgtaccaac agctccaact accagttgcc     780
tactgcctcg gaagcttaat aaaggatctt ttatttttcat tggctagctg tagaactcca     840
gcttcggcct gtcgcccaat caaactgtcc tgttactgaa tcgactgctg ttgaagtgag     900
cgccgtggta gttggagctc gtgtagtgaa gccacagatg tacacgagct ccaactacca     960
cgttgcctac tgcctcggaa gcaaaagtct gtagaaaagt aagggaaact caaacccgct    1020
gttgaagtga gcgccgtggt agtactagct agtgtagtga gccacagat gtacacgagc     1080
tccaactacc acgttgccta ctgcctcgga agcttaataa aggatctttt attttcattg    1140
gctggggatt gtgaccagaa gattttgaaa attaaatatt actgaagatt tcgacttcca    1200
ctgttaaatg tacaagatac atgaaatatt aagaaaatg tgtaacttt tgtgtaaata      1260
catcttgtgc ggccgcggat                                                 1280

<210> SEQ ID NO 54
<211> LENGTH: 1280
<212> TYPE: DNA
<213> ORGANISM: Homo sapiens

<400> SEQUENCE: 54

```
cgtcgtcgac tttcttcccc attagggatt atgctgaatt tgtatggttt atagttgtta      60
gagtttgagg tgttaattct aattatctat ttcaaattta gcaggaaaaa agagaacatc     120
accttgtaaa actgaagatt gtgaccatcg actgctgttg aagtgagcgc ctgtggtagt     180
tggagcttgt tagtgaagcc acagatgtaa caagctccaa ctaccacagt tgcctactgc     240
ctcggaagca gctgcctcgg aagccaagt tgggctttaa agtgcagggc tgctgatgt      300
tgagtgcttt tgctgttgaa gtgagcgcct gtggtagact gagctagtta gtgaagccac     360
agatgtaaca agctccaact accacagttg cctactgcct cggaagctta ataaaggatc     420
ttttatttc attggctaag aagttatgta ttcatccaat aattcaagcc aagcaagtat     480
ataggtgttt taatagtttt tgttttcgac tgctgttgaa gtgagcgccg tggtagttgg     540
agctgatgta gtgaagccac agatgtacat cagctccaac taccacgttg cctactgcct     600
cggaagctat ttccttcaaa tgaatgattt ttactaattt tgtgtacttt tattgtgtcg     660
atgtagaatc tgcctggtct atctgatgtg acagcttctg ctgttgaagt gagcgccgtg     720
gtagtcttag ctaatgtagt gaagccacag atgtacatca gctccaacta ccacgttgcc     780
tactgcctcg gaagcttaat aaaggatctt ttattttcat tggctagctg tagaactcca     840
gcttcggcct gtcgcccaat caaactgtcc tgttactgaa tcgactgctg ttgaagtgag     900
cgcctggtag ttggagctgt tggtagtgaa gccacagatg taccaacagc tccaactacc     960
agttgcctac tgcctcggaa gcaaaagtct gtagaaaagt aagggaaact caaacccgct    1020
gttgaagtga gcgcctggta gttactgcta ttggtagtga agccacagat gtaccaacag    1080
ctccaactac cagttgccta ctgcctcgga agcttaataa aggatctttt attttcattg    1140
gctggggatt gtgaccagaa gattttgaaa attaaatatt actgaagatt tcgacttcca    1200
ctgttaaatg tacaagatac atgaaatatt aagaaaatg tgtaacttt tgtgtaaata     1260
catcttgtgc ggccgcggat                                                1280
```

<210> SEQ ID NO 55
<211> LENGTH: 1029
<212> TYPE: DNA
<213> ORGANISM: Homo sapiens

<400> SEQUENCE: 55

```
cgtcgtcgac tttcttcccc attagggatt atgctgaatt tgtatggttt atagttgtta      60
gagtttgagg tgttaattct aattatctat ttcaaattta gcaggaaaaa agagaacatc     120
accttgtaaa actgaagatt gtgaccagtc agaataatgt gtggtagttg gagctgatgt     180
gatatgtgca tctcatcagc tccaactacc accattatgg tgacagctgc tcgggaagc     240
caagttgggc tttaaagtgc agggcctgct gatgttgagt gcttttgtt cgtggtagtc     300
ttagctaatg tgaagtagat tagcatctca tcagctccaa ctaccaccat aagaagttat     360
gtattcatcc aataattcaa gccaagcaag tatataggtg ttttaatagt ttttgtttgc     420
agtcctctgt ttggtagttg gagctgttgg agaagaatgt agtccaacag ctccaactac     480
catggtggcc tgctatttcc ttcaaatgaa tgatttttac taattttgtg tacttttatt     540
gtgtcgatgt agaatctgcc tggtctatct gatgtgacag cttctgtagc acttggtagt     600
```

```
tactgctatt ggtgtttagt tatctccaac agctccaact accatactgc tagctgtaga      660
actccagctt cggcctgtcg cccaatcaaa ctgtcctgtt actgaacact gttctatggt      720
tgtggtagtt ggagctcgtg tgtgtgatat tctgccacga gctccaacta ccacctgtgg      780
tagtgaaaag tctgtagaaa agtaagggaa actcaaaccc ctttctacac gtggtagtac      840
tagctagtgg tgtttctgta tggcacgagc tccaactacc actgagtttg gtggggattg      900
tgaccagaag attttgaaaa ttaaatatta ctgaagattt cgacttccac tgttaaatgt      960
acaagataca tgaaatatta agaaaatgt gtaacttttt gtgtaaatac atcttgtgcg     1020
gccgcggat                                                            1029

<210> SEQ ID NO 56
<211> LENGTH: 1029
<212> TYPE: DNA
<213> ORGANISM: Homo sapiens

<400> SEQUENCE: 56
cgtcgtcgac tttcttcccc attagggatt atgctgaatt tgtatggttt atagttgtta       60
gagtttgagg tgttaattct aattatctat ttcaaattta gcaggaaaaa agagaacatc      120
accttgtaaa actgaagatt gtgaccagtc agaataatgt tgtggtagtt ggagcttgtt      180
gatatgtgca tctacaagct ccaactacca cacattatgg tgacagctgc ctcgggaagc      240
caagttgggc tttaaagtgc agggcctgct gatgttgagt gcttttgttt ctgtggtaga      300
ctgagctagt tgaagtagat tagcatctac aagctccaac taccacacat aagaagttat      360
gtattcatcc aataattcaa gccaagcaag tatataggtg ttttaatagt ttttgtttgc      420
agtcctctgt tgtggtagtt ggagctgatg agaagaatgt agtcatcagc tccaactacc      480
actggtggcc tgctatttcc ttcaaatgaa tgattttac taattttgtg tacttttatt      540
gtgtcgatgt agaatctgcc tggtctatct gatgtgacag cttctgtagc actgtggtag      600
tcttagctaa tgtgtttagt tatctcatca gctccaacta ccactactgc tagctgtaga      660
actccagctt cggcctgtcg cccaatcaaa ctgtcctgtt actgaacact gttctatggt      720
ttggtagttg gagctgttgg tgtgtgatat tctgcccaac agctccaact accactgtgg      780
tagtgaaaag tctgtagaaa agtaagggaa actcaaaccc ctttctacac tggtagttac      840
tgctattggg tgtttctgta tggccaacag ctccaactac catgagtttg gtggggattg      900
tgaccagaag attttgaaaa ttaaatatta ctgaagattt cgacttccac tgttaaatgt      960
acaagataca tgaaatatta agaaaatgt gtaacttttt gtgtaaatac atcttgtgcg     1020
gccgcggat                                                            1029

<210> SEQ ID NO 57
<211> LENGTH: 1050
<212> TYPE: DNA
<213> ORGANISM: Homo sapiens

<400> SEQUENCE: 57
tttcttcccc attagggatt atgctgaatt tgtatggttt atagttgtta gagtttgagg       60
tgttaattct aattatctat ttcaaattta gcaggaaaaa agagaacatc accttgtaaa      120
actgaagatt gtgaccagtc agaataatgt caaagtgctt acagtgcagg tagtgatatg      180
tgcatctact gcagtgaagg cacttgtagc attatggtga cagctgcctc gggaagccaa      240
gttgggcttt aaagtgcagg gcctgctgat gttgagtgct tttgttcta aggtgcatct      300 agtgcagata gtgaagtaga ttagcatcta ctgccctaag tgctccttct ggcataagaa      360
```

```
gttatgtatt catccaataa ttcaagccaa gcaagtatat aggtgtttta atagtttttg      420
tttgcagtcc tctgttagtt ttgcatagtt gcactacaag aagaatgtag ttgtgcaaat      480
ctatgcaaaa ctgatggtgg cctgctattt ccttcaaatg aatgattttt actaattttg      540
tgtactttta ttgtgtcgat gtagaatctg cctggtctat ctgatgtgac agcttctgta      600
gcactaaagt gcttatagtg caggtagtgt ttagttatct actgcattat gagcacttaa      660
agtactgcta gctgtagaac tccagcttcg gcctgtcgcc caatcaaact gtcctgttac      720
tgaacactgt tctatggtta gttttgcagg tttgcatcca gctgtgtgat attctgctgt      780
gcaaatccat gcaaaactga ctgtggtagt gaaaagtctg tagaaaagta agggaaactc      840 aaacccettt ctacacaggt tgggatcggt tgcaatgctg tgtttctgta tggtattgca      900
cttgtcccgg cctgttgagt ttggtgggga ttgtgaccag aagattttga aaattaaata      960
ttactgaaga tttcgacttc cactgttaaa tgtacaagat acatgaaata ttaaagaaaa     1020
tgtgtaactt tttgtgtaaa tacatcttgt                                      1050

<210> SEQ ID NO 58
<211> LENGTH: 51
<212> TYPE: DNA
<213> ORGANISM: Homo sapiens

<400> SEQUENCE: 58
atgactgaat ataaacttgt ggtagttgga gctggtggcg taggcaagag t                51
```